(12) United States Patent
Lebel et al.

(10) Patent No.: US 7,030,294 B2
(45) Date of Patent: Apr. 18, 2006

(54) EXPRESSION OF TREHALOSE 6-PHOSPHATE SYNTHASE AND TREHALOSE 6-PHOSPHATE PHOSPHATASE IN PLANT PLASTIDS

(75) Inventors: Edouard Guillaume Lebel, Research Triangle Park, NC (US); Peter Bernard Heifetz, San Diego, CA (US); Stephen Arthur Goff, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 402 days.

(21) Appl. No.: 10/648,984

(22) Filed: Aug. 27, 2003

(65) Prior Publication Data

US 2004/0078848 A1    Apr. 22, 2004

Related U.S. Application Data

(62) Division of application No. 09/894,799, filed on Jun. 28, 2001, now Pat. No. 6,686,516, which is a division of application No. 09/262,615, filed on Mar. 4, 1999, now abandoned.

(60) Provisional application No. 60/077,665, filed on Mar. 11, 1998.

(51) Int. Cl.
*C12N 15/82* (2006.01)

(52) U.S. Cl. .................................................. 800/298

(58) Field of Classification Search ...................... None
See application file for complete search history.

(56) References Cited

U.S. PATENT DOCUMENTS

| 5,422,254 | A |   | 6/1995  | Londesborough et al. .... 435/97 |
|-----------|---|---|---------|----------------------------------|
| 5,693,507 | A | * | 12/1997 | Daniell et al. .............. 435/470 |
| 5,792,921 | A |   | 8/1998  | Londesborough et al. .. 800/205 |

FOREIGN PATENT DOCUMENTS

| WO | 9317093    | 9/1993  |
|----|------------|---------|
| WO | WO 95/01446 | 1/1995  |
| WO | 9514098    | 5/1995  |
| WO | 9524492    | 9/1995  |
| WO | WO 96/00789 | 1/1996  |
| WO | WO 97/42327 | 11/1997 |
| WO | 9803536    | 1/1998  |

OTHER PUBLICATIONS

Blazquez, M. A. et al., "Isolation and molecular characterization of the Arabidopsis TPS1 gene, encoding trehalose-6-phosphate synthase," Plant Journal, 13(5): pp685-689 (1998).

Goddijn, O. J. M. et al. "Inhibition of Trehalose Activity Enhances Trehalose Accumulation in Transgenic Plants," Plant Physiology, 113: pp181-190 (1997).

Holmstrom, K-O., "Drought tolerance in tobacco," Nature, 379: pp683-684 (1996).

Kaasen, I. et al., "Analysis of the otsBA operon for osmoregulatory trehalose synthesis in *Escherichia coli* and homology of the OtsA and OtsB proteins to the yeast trehalose-6-phosphate synthase/phosphatase complex," Gene, 145: pp9-15 (1994).

Kassen, I. et al., "Molecular Cloning and Physical Mapping of the otsBA Genes, Which Encode the Osmoregulatory Trehalose Pathway of *Eschrichia coli*: Evidence that Transcription Is Activated by KatF (AppR)," Journal of Bacteriology, 174(3): pp889-898 (1992).

Lebel, E. et al., "Chemical Regulation of Transgene Expression in Plants," Abstract for Biochemical Society Symposium: Engineering Crops for Industrial Ends in Bristol, UK (1996).

Muller, J. et al., "Pools of non-structural carbohydrates in soybean root nodules during water stress," Physiologia Plantarum, 98: pp723-730 (1996).

Muller, J. et al., "Trehalose and trehalase in plants: recent developments," Plant Science, 112:pp1-9 (1995).

Pilon-Smits, E. A. H. et al., "Trehalose-Producing Transgenic Tobacco Plants Show Improved Growth Performance Under Drought Stress," Journal of Plant Physiology, 152:pp. 525-532 (1998).

Romero, C. et al., "Expression of yeast trehalose-6-phosphate synthase gene in transgenic tobacco plants: pleiotropic phenotypes include drought tolerance," Planta, 201: pp293-297 (1997).

Salminen, S. O. et al., "Enzymes of a,a-Trehalose Metabolism in Soybean Nodules," Plant Physiology, 81: pp538-541.

Vogel, G. et al., "Trehalose-6-phosphate phosphatases from *Arabidopsis thaliana*: identification by functional complementation of the yeast tps2 mutant," Plant Journal, 13(5): pp673-683 (1998).

Vuorio, O. E. et al., "Cloning of two related genes encoding the 56-kDa and 123-kDa subunits of trehalose synthase from the yeast *Saccharomyces cerevisiae*," Eur. Journal of Biochemistry, 216:849-861 (1993).

Heifetz et al., Plant Physiology, 114(3):308 Aug. 1997.

* cited by examiner

*Primary Examiner*—Anne Kubelik
(74) *Attorney, Agent, or Firm*—Mary Kakefuda

(57) ABSTRACT

The invention provides novel stress tolerant transgenic plants which express trehalose 6-phosphate synthase and trehalose-6-phosphate phosphatase in their plastids.

3 Claims, No Drawings

SEQUENCE LISTING

<160> NUMBER OF SEQ ID NOS: 38

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: oligonucleotide

<400> SEQUENCE: 1
gtcagccatg gcaagtcgtt tagtcgtagt atctaac    37

```
<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
gcaaatggca acaggtgata atcg                                              24

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gtcagccatg gtgacagaac cgttaaccga aac                                    33

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
gtgcgtcaag ctccaccatt gagc                                              24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
taacggccgc gcccaatcat tccggata                                          28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
taactgcaga aagaaggccc ggctccaa                                          28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
cgcctgcagt cgcactatta cggatatg                                          28

<210> SEQ ID NO 8
```

```
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
cgccgtacga aatccttccc gatacctc                                28

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
gccagaattc gccgtcgttc aatgagaatg                              30

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
gccttcatga tccctcccta caactatcca ggcgcttcag attcg              45

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
cgcgactagt tcaaccgaaa ttcaat                                   26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
cgctctgcag ttcaatggaa gcaatg                                   26

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
accgtaaggc ttgatgaa                                            18

<210> SEQ ID NO 14
<211> LENGTH: 27
```

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
cccactagtt tgaacgaatt gttagac                                           27

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
cccgaattca tcccgcgaaa ttaata                                            26

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
cggccatggg tatatctcct tcttaaagtt aaa                                    33

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
gcgaagcttg ctgagcaata actagcataa                                        30

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
gcgctgcagt ccggatatag ttcctcct                                          28

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
gcgactagtt agtgttagtc taaatctagt t                                      31

<210> SEQ ID NO 20
<211> LENGTH: 30
<212> TYPE: DNA
```

```
<213> ORGANISM: Artificial Sequence
<220> FEATURE:
<223> OTHER INFORMATION: Description of Artificial Sequence:
      oligonucleotide

<400> SEQUENCE: 20
ccgcaagctt ctaataaaaa atatatagta                                    30

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
ctagtggggg ggggggggggg ggga                                         24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
agcttccccc cccccccccc ccca                                          24

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
tgaccatggc aagtcgttta gtcgtagt                                      28

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
agcaacgctt catag                                                    15

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
gcgttcctgg attgtc                                                   16

<210> SEQ ID NO 26
<211> LENGTH: 37
<212> TYPE: DNA
<213> ORGANISM: Artificial Sequence
```

```
<220> FEATURE:
<223> OTHER INFORMATION: Description of Artificial Sequence:
      oligonucleotide

<400> SEQUENCE: 26
gggtctagag attcacgcga gctttggaaa ggtagca                                37

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gtcgccatgg tgacagaacc gttaacc                                           27

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
gttcgcccga taaagggag                                                    19

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
tagcgcaacg tattactc                                                     18

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
gcctctagac tcatcattag atactacgac taaac                                  35

<210> SEQ ID NO 31
<211> LENGTH: 67
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
ctagtgggag accacaacgg tttccctcta gaaataattt tgtttaagtt taagaagggg       60
agagaat                                                                 67

<210> SEQ ID NO 32
<211> LENGTH: 67
<212> TYPE: DNA
```

```
<213> ORGANISM: Artificial Sequence
<220> FEATURE:
<223> OTHER INFORMATION: Description of Artificial Sequence:
      oligonucleotide

<400> SEQUENCE: 32
catgattctc tcccttctt aaacttaaac aaaattattt ctagagggaa accgttgtgg    60
tctccca                                                             67

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
gcggaattca tacttattta tcattagaaa g                                  31

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
gcgccatggt aaatgaaaga aagaactaaa                                    30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
gcgtctagat caaccgaaat tcaattaagg                                    30

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
cgcaagcttc aatggaagca atgataa                                       27

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
catggcttcc tcagttcttt cctctgca                                      28

<210> SEQ ID NO 38
<211> LENGTH: 20
```

-continued

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
gaggaaagaa ctgaggaagc                                                   20
```

EXPRESSION OF TREHALOSE 6-PHOSPHATE SYNTHASE AND TREHALOSE 6-PHOSPHATE PHOSPHATASE IN PLANT PLASTIDS

CROSS-REFERENCE TO RELATED APPLICATIONS

This application claims the benefit of U.S. Provisional Application No. 60/077,665, filed Mar. 11, 1998. The above application is incorporated herein by reference.

FIELD OF THE INVENTION

The invention relates to expression of trehalose biosynthetic genes and drought resistance in plants.

BACKGROUND OF THE INVENTION

Trehalose (a-D-glucopyranosyl-[1,1]-a-D-glucopyranoside) is a disaccharide commonly found in lower organisms such as bacteria, fungi and insects where it often accumulates in resting or stationary phase cells and organs. Two enzymatic activities are required for trehalose biosynthesis: a trehalose-6-phosphate synthase catalyses the condensation of UDP-glucose and glucose-6-phosphate to trehalose-6-phosphate and a trehalose-6-phosphate phosphatase phosphorylates trehalose-6-phosphate to trehalose.

Although trehalose can serve as a storage form for reduced carbon, it may play a more significant role as a protectant against the deleterious effects of various abiotic stresses, notably heat and desiccation. Both in vivo and in vitro, trehalose accumulation is correlated with protection of biological macromolecules (particularly membranes and proteins) from dessication, temperature extremes, and osmotic shock. Trehalose produced by fermentation is used commercially in the preservation of enzymes and is registered as a food additive for the stabilization of dehydrated and processed foods.

While it has long been recognized that trehalose may occur in plants as a product of symbiotic microorganisms, as a rule vertebrates and higher plants were thought not to be capable of synthesizing trehalose. The near-ubiquitous occurrence of specific trehalose-catabolizing enzymes (trehalases) in higher plant families was a biological curiousity ascribed mainly to the presence of exogenous trehalose entering plant cells from symbiotic or epiphytic microbial and fungal sources. Notable exceptions are the lower plants and angiosperms grouped loosely into the category of "resurrection plants" which are capable of surviving extraordinarily prolonged periods of dessication. These plants, including species of *Selaginella* and *Myrothamnus*, can accumulate as much as 10% trehalose by dry weight following the onset of droughting.

In view of trehalose's association with drought resistance and the historically poor economics of microbial trehalose fermentation, attempts have also been made to engineer transgenic plants to accumulate this disaccharide. Although such plants have been obtained, it has become apparent that constitutive trehalose production in the plant cytosol is accompanied by significant deleterious effects. These phenotypes (stunted growth, abnormal leaves, undeveloped roots) are particulary severe when trehalose expression occurs in root tissue or during early development, as the use of green-tissue specific plant promoters to drive trehalose producing genes ameliorates some, but not all, of these effects.

Given these facts, an inducible expression system for the trehalose biosynthetic genes, which allows for trehalose accumulation and results in drought resistance but without deleterious effects to the plant is of great practical use and economic interest.

SUMMARY OF THE INVENTION

The present invention thus relates to expression of trehalose biosynthetic genes and drought resistance in plants. In particular, this invention addresses the issue of trehalose accumulation and drought resistance in higher plants and novel ways to engineer such trait. It also addresses the need for improved storage properties of harvested plants, improved shelf-life of fruits and flowers, as well as stabilization of foreign proteins expressed in transgenic plants. In a prefered embodiment, the invention describes the expression of the trehalose biosynthetic genes in plants, preferably under the control of an inducible promoter, which allow for drought resistance without the deleterious effect associated with uncontrolled accumulation of trehalose. A prefered promoter is a chemically inducible promoter, such as the tobacco PR-1a promoter, which can be activated by foliar application of a chemical inducer.

Additionally, the invention describes expression of the trehalose biosynthetic genes expressed in different cellular compartments. In a first embodiment the trehalose biosynthetic genes are expressed in the plant cytoplasm. In a further embodiment, the trehalose biosynthetic genes are expressed from the plant nuclear genome and the trehalose biosynthetic enzymes encoded therefrom are targeted to the plastids, e.g. by using a plastid transit peptide. In a further embodiment, the trehalose biosynthetic genes are expressed from the plant plastid genome. In a preferred embodiment, vectors containing the trehalose biosynthetic genes fused to a promoter capable of directing the expression of the trehalose biosynthetic genes in plant plastids are transformed into the plastid genome. In a preferred embodiment, vectors containing a phage promoter fused to the trehalose biosynthetic genes are transformed into the plastid genome. The resulting line is crossed to a transgenic line containing a nuclear coding region for a phage RNA polymerase supplemented with a plastid-targeting sequence and operably linked to a plant promoter, such as an inducible promoter, a tissue-specific promoter or a constitutive promoter. In another preferred embodiment, a promoter capable of directing the expression of the trehalose biosynthetic genes in plant plastids is a promoter transcribed by a RNA polymerase normally present in plastids, such as a nuclear-encoded polymerase or a plastid-encoded polymerase. Such promoters are e.g. but not limited to a clpP promoter, a 16S r-RNA gene promoter, a psbA promoter or a rbcL promoter.

In the present invention, trehalose biosynthetic genes from *E. coli* are preferably used, but trehalose biosynthetic genes from other organisms including but not limited to yeast, other lower organisms or higher organisms, such as plants, are suitable. In a preferred embodiment, a nucleotide sequence encoding a trehalose phosphate synthase and a nucleotide sequence encoding a trehalose phosphate phosphatase are both expressed in the plant. In another preferred embodiment, a nucleotide sequence encoding a trehalose phosphate synthase is expressed in the plant, or a nucleotide sequence encoding a trehalose phosphate phosphatase is expressed in the plant. The present invention also relates to the expression from the plastid genome of two trehalose biosynthetic genes transcribed from a single promoter in an operon-like polycistronic gene.

The Invention thus Provides:

A plant expressing a nucleotide sequence encoding a trehalose biosynthetic enzyme, for example a plant comprising nucleotide sequence coding for the trehalose 6-phosphate synthase and/or trehalose 6-phosphate phosphatase, for example the *E. coli* OtsA and/or *E.coli* OtsB genes. Such nucleotide sequences are for example stably integrated in its nuclear or plastid genome, under the control of a promoter capable of directing the expression of the trehalose biosynthetic genes in said plant, e.g. under the control of an inducible promoter, e.g., a wound-inducible or chemically inducible promoter, such as the tobacco PR-1a promoter or *Arabidopsis* PR-1 promoter, or, a transactivator-regulated promoter wherein the corresponding transactivator is under the control of a promoter capable of directing the expression of the transactivator in said plant, e.g. an inducible promoter, a tissue-specific promoter or a constitutive promoter, e.g., a wound-inducible or chemically inducible promoter, such as the tobacco PR-1a promoter or *Arabidopsis* PR-1 promoter;

also including the seed for such a plant, which seed is optionally treated (e.g., primed or coated) and/or packaged, e.g. placed in a bag with instructions for use. In particular, the invention provides:

A plant comprising in its nuclear genome a first heterologous expression cassette or parts thereof comprising a nucleotide sequence encoding a trehalose 6-phosphate synthase under control of an inducible promoter and a second heterologous expression cassette or parts thereof comprising a nucleotide sequence encoding a trehalose-6-phosphate phosphatase under control of an inducible promoter. also including the seed for such a plant, which seed is optionally treated (e.g., primed or coated) and/or packaged, e.g. placed in a bag with instructions for use.

The Invention Further Provides:

A plant comprising in its plastid genome a first heterologous expression cassette or parts thereof comprising a nucleotide sequence encoding a trehalose 6-phosphate synthase under control of a promoter capable of directing the expression of the nucleotide sequence in the plastids of said plant, e.g. a transactivator-regulated promoter wherein the corresponding transactivator is preferably under the control of an inducible promoter, a tissue-specific promoter or a constitutive promoter, and a second heterologous expression cassette or parts thereof comprising a nucleotide sequence encoding a trehalose-6-phosphate phosphatase under control of a promoter capable of directing the expression of the nucleotide sequence in the plastids of said plant, e.g. a transactivator-regulated promoter wherein the corresponding transactivator is preferably under the control of an inducible promoter, a tissue-specific promoter or a constitutive promoter.

also including the seed for such a plant, which seed is optionally treated (e.g., primed or coated) and/or packaged, e.g. placed in a bag with instructions for use.

The invention further provides:

A heterologous plant nuclear expression cassette comprising a nucleotide sequence encoding a trehalose-6-phosphate synthase, preferably under the control of an inducible promoter, e.g., a wound inducible or chemically inducible promoter;

a vector comprising such plant expressible cassette; and a plant transformed with such a vector.

The invention further provides:

A heterologous plant nuclear expression cassette comprising a nucleotide sequence encoding a trehalose-6-phosphate phosphatase, preferably under the control of an inducible promoter, e.g., a wound inducible or chemically inducible promoter;

a vector comprising such plant expressible cassette; and a plant transformed with such a vector.

The invention further provides:

A heterologous plant expression cassette comprising a nucleotide sequence encoding a trehalose-6-phosphate synthase, preferably under the control of an inducible promoter, e.g., a wound inducible or chemically inducible promoter, and further comprising a nucleotide sequence encoding a trehalose-6-phosphate phosphatase, preferably under the control of an inducible promoter, e.g., a wound inducible or chemically inducible promoter;

a vector comprising such plant expressible cassette; and a plant transformed with such a vector.

In a further embodiment, the invention encompasses expression of nucleotide sequences encoding trehalose biosynthetic enzymes in plastids under the control of a promoter capable of directing the expression of a nucleotide sequence in the plastids of a plant, e.g. a transactivator-regulated promoter, and the gene for the transactivator is in the nuclear DNA, under the control of an plant promoter. For example, plastid transformation vectors are typically constructed using a phage promoter, such as the phage T7 gene 10 promoter, the transcriptional activation of which is dependent upon an RNA polymerase such as the phage T7 RNA polymerase. The resulting line is crossed to a transgenic line containing a nuclear coding region for a phage RNA polymerase supplemented with a chloroplast-targeting sequence and operably linked to a plant promoter, preferably an inducible promoter, a tissue-specific promoter or a constitutive promoter, preferably a chemically inducible promoter such as the tobacco PR-1a promoter.

The Invention thus Additionally Provides:

A Plant Comprising a heterologous plastid expression cassette or parts thereof comprising a nucleotide sequence encoding at least one trehalose biosynthetic enzyme such as, for example, a trehalose-6-phosphate synthase or a trehalose-6-phosphate phosphatase under the control of a promoter capable of directing the expression of a nucleotide sequence in the plastids of a plant; also including the seed for such a plant, which seed is optionally treated (e.g., primed or coated) and/or packaged, e.g. placed in a bag or other container with instructions for use.

A Plant Comprising a heterologous nuclear expression cassette or parts thereof preferably comprising an inducible promoter, a tissue-specific promoter or a constitutive promoter, more preferably an inducible promoter, e.g., a wound-inducible or chemically-inducible promoter, for example the tobacco PR-1a promoter, operably linked to a DNA sequence coding for a transactivator (preferably a transactivator not naturally occurring in plants, preferably a RNA polymerase or DNA binding protein, e.g., T7 RNA polymerase), said transactivator being optionally fused to a plastid targeting sequence, e.g., a chloroplast targeting sequence (e.g., a plant expressible expression cassette as described above); and a heterologous plastid expression cassette or parts thereof comprising a transactivator-mediated promoter regulated by the transactivator (e.g., the T7 promoter when the transactivator is T7 RNA polymerase) and operably linked to a nucleotide sequence encoding at least one trehalose biosynthetic enzyme such as, for example, a trehalose-6-phosphate synthase; also including the seed for such a plant, which seed is optionally treated (e.g., primed or coated) and/or packaged, e.g. placed in a bag or other container with instructions for use.

The Invention Furthermore Provides:

A Plant Comprising a heterologous nuclear expression cassette or parts thereof preferably comprising an inducible promoter, a tissue-specific promoter or a constitutive promoter, more preferably an inducible promoter, e.g., a wound-inducible or chemically-inducible promoter, for example the tobacco PR-1a promoter, operably linked to a nucleotide sequence encoding a transactivator (preferably a transactivator not naturally occurring in plants, preferably a RNA polymerase or DNA binding protein, e.g., T7 RNA polymerase), said transactivator being optionally fused to a plastid targeting sequence, e.g., a chloroplast targeting sequence (e.g., a plant expressible expression cassette as described above); and a heterologous plastid expression cassette or parts thereof comprising a transactivator-mediated promoter regulated by the transactivator (e.g., the T7 promoter when the transactivator is T7 RNA polymerase) and operably linked to a nucleotide sequence encoding a trehalose-6-phosphate phosphatase;

also including the seed for such a plant, which seed is optionally treated (e.g., primed or coated) and/or packaged, e.g. placed in a bag or other container with instructions for use.

The Invention Furthermore Provides:

A Plant Comprising a heterologous nuclear expression cassette or parts thereof preferably comprising an inducible promoter, a tissue-specific promoter or a constitutive promoter, more preferably an inducible promoter, e.g., a wound-inducible or chemically-inducible promoter, for example the tobacco PR-1a promoter, operably linked to a DNA sequence coding for a transactivator (preferably a transactivator not naturally occurring in plants, preferably a RNA polymerase or DNA binding protein, e.g., T7 RNA polymerase), said transactivator being optionally fused to a plastid targeting sequence, e.g., a chloroplast targeting sequence (e.g., a plant expressible expression cassette as described above); and a heterologous plastid expression cassette or parts thereof comprising a transactivator-mediated promoter regulated by the transactivator (e.g., the T7 promoter when the transactivator is T7 RNA polymerase) and operably linked to a nucleotide sequence encoding a trehalose-6-phosphate synthase and a transactivator-mediated promoter regulated by the transactivator (e.g., the T7 promoter when the transactivator is T7 RNA polymerase) and operably linked to a nucleotide sequence encoding a trehalose-6-phosphate phosphatase;

also including the seed for such a plant, which seed is optionally treated (e.g., primed or coated) and/or packaged, e.g. placed in a bag or other container with instructions for use.

In a further embodiment the invention encompasses expression of nucleotide sequences encoding trehalose biosynthetic in the plastid under the control of a promoter transcribed by a RNA polymerase normally present in plastids, such as a nuclear-encoded polymerase or a plastid-encoded polymerase. Such promoters are e.g., but not limited to, a clpP promoter, a 16S r-RNA gene promoter, a psbA promoter or a rbcL promoter.

The Invention thus Additionally Provides:

A Plant Comprising a heterologous plastid expression cassette or parts thereof preferably comprising a promoter capable of expression of a nucleotide sequence encoding trehalose biosynthetic enzymes in plant plastids, for example a promoter transcribed by a RNA polymerase normally present in plastids, such as a nuclear-encoded polymerase or a plastid-encoded polymerase, operably linked to at least a nucleotide sequence encoding a trehalose biosynthetic enzyme such as, for example, a trehalose-6-phosphate synthase; also including the seed for such a plant, which seed is optionally treated (e.g., primed or coated) and/or packaged, e.g. placed in a bag or other container with instructions for use.

The Invention Furthermore Provides:

A Plant Comprising a heterologous plastid expression cassette or parts thereof preferably comprising a promoter capable of expression of a nucleotide sequence encoding a trehalose biosynthetic enzyme in plant plastids, for example a promoter transcribed by a RNA polymerase normally present in plastids, such as a nuclear-encoded polymerase or a plastid-encoded polymerase, operably linked to a nucleotide sequence encoding a trehalose-6-phosphate phosphatase;

also including the seed for such a plant, which seed is optionally treated (e.g., primed or coated) and/or packaged, e.g. placed in a bag or other container with instructions for use.

The Invention Furthermore Provides:

A Plant Comprising a heterologous plastid expression cassette or parts thereof preferably comprising a promoter capable of expression of a nucleotide sequence encoding a trehalose biosynthetic enzyme in plant plastids, for example a promoter transcribed by a RNA polymerase normally present in plastids, such as a nuclear-encoded polymerase or a plastid-encoded polymerase, operably linked to a nucleotide sequence encoding a trehalose-6-phosphate synthase and a promoter transcribed by a RNA polymerase normally present in plastids, such as a nuclear-encoded polymerase or a plastid-encoded polymerase, operably linked to a nucleotide sequence encoding a trehalose-6-phosphate phosphatase;

also including the seed for such a plant, which seed is optionally treated (e.g., primed or coated) and/or packaged, e.g. placed in a bag or other container with instructions for use.

In a further embodiment, the invention encompasses the expression from a single promoter of two or more genes in plant plastids in an operon-like polycistronic gene. In a preferred embodiment, an operon-like polycistronic gene comprises the two or more genes, e.g. genes comprising a nucleotide sequence encoding a trehalose biosynthetic enzyme, operably linked to a promoter capable of directing the expression of operon-like polycistronic gene in plastids and is inserted into the plastid genome. In a preferred embodiment, the operon-like polycistronic gene comprises an intervening DNA sequence between two genes in the operon-like polycistronic gene, preferably a DNA sequence not present in the plastid genome. In another preferred embodiment, the intervening DNA sequence is derived from the 5' untranslated (UTR) region of a non-eukaryotic gene, preferably a viral 5'UTR, preferably a 5'UTR derived from a bacterial phage, such as a T7, T3 or SP6 phage. In a preferred embodiment, the DNA sequence is modified to prevent the formation of secondary structures that inhibit or repress translation of the gene located immediately downstream of the intervening DNA sequence. In a preferred embodiment, the expression, preferably the translation, of genes located immediately downstream of the intervening DNA sequence is increased.

The Invention thus Furthermore Provides:

A Plant Comprising a heterologous nuclear expression cassette or parts thereof preferably comprising an inducible promoter, a tissue-specific promoter or a constitutive promoter, more preferably an inducible promoter, e.g., a wound-inducible or chemically-inducible promoter, for example the tobacco PR-1a promoter, operably linked to a nucleotide sequence encoding a transactivator (preferably a transactivator not naturally occurring in plants, preferably a RNA polymerase or DNA binding protein, e.g., T7 RNA polymerase), said transactivator being optionally fused to a plastid targeting sequence, e.g., a chloroplast targeting sequence (e.g., a plant expressible expression cassette as described above); and a heterologous plastid expression cassette or parts thereof comprising a transactivator-mediated promoter regulated by the transactivator (e.g., the T7 promoter when the transactivator is T7 RNA polymerase) and operably linked to an operon-like polycistronic gene comprising at least one gene comprising a nucleotide sequence encoding a trehalose biosynthetic enzyme. In a preferred embodiment, the operon-like polycistronic gene comprises one gene comprising a nucleotide sequence encoding a trehalose phosphate synthase and one gene encoding a nucleotide sequence encoding a trehalose phosphate phosphatase. In a preferred embodiment, the operon-like polycistronic gene comprises an intervening DNA sequence between two genes in the operon-like polycistronic gene, preferably a DNA sequence not present in the plastid genome. In a preferred embodiment, the DNA sequence is derived from the 5' untranslated (UTR) region of a non-eukaryotic gene, preferably a viral 5'UTR, preferably a 5'UTR derived from a bacterial phage, such as a T7, T3 or SP6 phage. In a preferred embodiment, the DNA sequence is modified to prevent the formation of secondary structures that inhibit or repress translation of the gene located immediately downstream of the intervening DNA sequence. In a preferred embodiment, the expression, preferably the translation, of genes located immediately downstream of the intervening DNA sequence is increased.

also including the seed for such a plant, which seed is optionally treated (e.g., primed or coated) and/or packaged, e.g. placed in a bag or other container with instructions for use.

The Invention Furthermore Provides:

A Plant Comprising a heterologous nuclear expression cassette or parts thereof preferably comprising a promoter capable of expression of a nucleotide sequence encoding a trehalose biosynthetic enzyme in plant plastids, for example a promoter transcribed by a RNA polymerase normally present in plastids, such as a nuclear-encoded polymerase or a plastid-encoded polymerase, operably linked to an operon-like polycistronic gene comprising at least one gene comprising a nucleotide sequence encoding a trehalose biosynthetic enzyme. In a preferred embodiment, the operon-like polycistronic gene comprises one gene comprising a nucleotide sequence encoding a trehalose phosphate synthase and one gene encoding a nucleotide sequence encoding a trehalose phosphate phosphatase. In a preferred embodiment, the operon-like polycistronic gene comprises an intervening DNA sequence between two genes in the operon-like polycistronic gene, preferably a DNA sequence not present in the plastid. In a preferred embodiment, the DNA sequence is derived from the 5' untranslated (UTR) region of a noneukaryotic gene, preferably a viral 5'UTR, preferably a 5'UTR derived from a bacterial phage, such as a T7, T3 or SP6 phage. In a preferred embodiment, the DNA sequence is modified to prevent the formation of secondary structures that inhibit or repress translation of the gene located immediately downstream of the intervening DNA sequence. In a preferred embodiment, the expression, preferably the translation, of genes located immediately downstream of the intervening DNA sequence is increased.

also including the seed for such a plant, which seed is optionally treated (e.g., primed or coated) and/or packaged, e.g. placed in a bag or other container with instructions for use.

The Invention Furthermore Provides:

A plant expressible expression cassette preferably comprising an inducible promoter, e.g., a wound-inducible or chemically-inducible promoter, for example the tobacco PR-1a promoter, operably linked to a nucleotide sequence encoding a transactivator (preferably a transactivator not naturally occurring in plants, preferably a RNA polymerase or DNA binding protein, e.g., T7 RNA polymerase), said transactivator being fused to a plastid targeting sequence, e.g., a chloroplast targeting sequence;

a vector comprising such a plant expressible cassette; and a plant transformed with such a vector or a transgenic plant the genome of which comprises such a plant expressible expression cassette.

The Invention also Provides:

A heterologous plastid expression cassette comprising a transactivator-mediated promoter regulated by the transactivator (e.g., the T7 promoter when the transactivator is T7 RNA polymerase) and operably linked to a nucleotide sequence encoding at least one trehalose biosynthetic enzyme such as, for example, a trehalose-6-phosphate synthase and/or a trehalose 6-phosphate phosphatase.

The Invention also Provides:

A heterologous plastid expression cassette comprising a promoter transcribed by a RNA polymerase normally present in plastids, such as a nuclear-encoded polymerase or a plastid-encoded polymerase and operably linked to a nucleotide sequence encoding at least one trehalose biosynthetic enzyme such as, for example, a trehalose-6-phosphate synthase and/or trehalose 6-phosphate phosphatase.

The Invention also Provides:

A heterologous plastid expression cassette comprising a promoter capable of expression of a trehalose biosynthetic gene in plant plastids, for example a promoter transcribed by a RNA polymerase normally present in plastids, such as a nuclear-encoded polymerase or a plastid-encoded polymerase, or a transactivator-mediated promoter regulated by the transactivator (e.g., the T7 promoter when the transactivator is T7 RNA polymerase), operably linked to an operon-like polycistronic gene comprising nucleotide sequences encoding both trehalose biosynthetic enzymes. In a preferred embodiment, the operon-like polycistronic gene comprises an intervening DNA sequence between two genes in the operon-like polycistronic gene, preferably a DNA sequence not present in the plastid genome. In a preferred embodiment, the DNA sequence is comprises a portion of the 5' untranslated (UTR) region of a non-eukaryotic gene, preferably a viral 5'UTR, preferably a 5'UTR derived from a bacterial phage, such as a T7, T3 or SP6 phage. In a preferred embodiment, the DNA sequence is modified to prevent the formation of secondary structures that inhibit or repress the translation of the gene located immediately downstream of the intervening DNA sequence. In a preferred embodiment, the expression, preferably the translation, of genes located immediately downstream of the intervening DNA sequence is increased.

The Invention also Comprises:

A Method of Producing a Plant as Described Above Comprising pollinating a plant comprising a heterologous plastid expression cassette or parts thereof comprising a transactivator-mediated promoter regulated and operably linked to a nucleotide sequence of interest, but preferably a nucleotide sequence encoding at least one trehalose biosynthetic enzyme such as, for example a trehalose-6-phosphate synthase and/or a trehalose 6-phosphate phosphatase with pollen from a plant comprising a heterologous nuclear expression cassette or parts thereof comprising an inducible promoter, a tissue-specific promoter or a constitutive promoter, more preferably an inducible promoter, operably linked to a nucleotide sequence encoding a transactivator capable of regulating said transactivator-mediated promoter;

recovering seed from the plant thus pollinated; and cultivating a plant as described above from said seed.

The Invention Further Provides:

A method for producing trehalose in a plant by expressing at least one heterologous nucleotide sequence encoding a trehalose biosynthetic enzyme under the control of any one of the promoters described above, for example an inducible promoter, e.g., a wound inducible or chemically inducible promoter, in the nuclear genome of said plant or by expressing at least one heterologous nucleotide sequence encoding a trehalose biosynthetic enzyme in the plastids of said plant under the control of a promoter capable of expressing said nucleotide sequence in the plastids of said plant or in any one of the expression cassettes described above.

A method for protecting a plant against drought, high salinity, osmotic stress and temperature extremes by expressing in said plant at least one nucleotide sequence encoding a trehalose biosynthetic enzyme from the nuclear genome of said plant under the control of an inducible promoter e.g., a wound inducible or chemically inducible promoter, or from the plastid genome of said plant under the control of a promoter capable of expressing said nucleotide sequence in the plastids of said plant.

A method for increasing storage properties of harvested plants by expressing in said plant at least one nucleotide sequence encoding a trehalose biosynthetic enzyme from the nuclear genome of said plant under the control of an inducible promoter e.g., a wound inducible or chemically inducible promoter, or from the plastid genome of said plant under the control of a promoter capable of expressing said nucleotide sequence in the plastids of said plant.

A method for improving shelf-life of fruits and vegetables, and preserving flowers by expressing in said fruits, vegetables and flowers at least one nucleotide sequence encoding a trehalose biosynthetic enzyme from the nuclear genome of said plant under the control of an inducible promoter e.g., a wound inducible or chemically inducible promoter, or from the plastid genome of said plant under the control of a promoter capable of expressing said nucleotide sequence in the plastids of said plant.

A method for stabilizing proteins, preferably transgenic proteins, expressed in transgenic plants by expressing in said plant at least one nucleotide sequence encoding a trehalose biosynthetic enzyme from the nuclear genome of said plant under the control of an inducible promoter e.g., a wound inducible or chemically inducible promoter, or from the plastid genome of said plant under the control of a promoter capable of expressing said nucleotide sequence in the plastids of said plant.

The Present Invention Further Provides:

A method of expressing two or more genes from a single promoter in the plastids of a plant comprising introducing into the plastid genome of said plant a operon-like polycistronic gene comprising said two or more genes operably linked to a promoter capable of expressing said operon-like polycistronic gene in the plastids of said plant, wherein said operon-like polycistronic gene further comprises an intervening DNA sequence between two genes. In a preferred embodiment, a DNA sequence not present in the plastid genome. In a preferred embodiment, the DNA sequence is comprises a portion of the 5' untranslated (UTR) region of a non-eukaryotic gene, preferably a viral 5'UTR, preferably a 5'UTR derived from a bacterial phage, such as a T7, T3 or SP6 phage. In a preferred embodiment, the DNA sequence is modified to prevent the formation of secondary structures that inhibit or repress the translation of the gene located immediately downstream of the intervening DNA sequence. In a preferred embodiment, the expression, preferably the translation, of genes located immediately downstream of the intervening DNA sequence is increased.

In a preferred embodiment, the operon-like polycistronic gene comprises at least one gene comprising a nucleotide sequence encoding a trehalose biosynthetic gene. In another preferred embodiment, the operon-like polycistronic gene comprises a gene comprising a nucleotide sequence encoding a trehalose phosphate synthase and a gene comprising a nucleotide sequence encoding a trehalose phosphate phosphatase.

DEFINITIONS

In order to ensure a clear and consistent understanding of the specification and the claims, the following definitions are provided:

"Drought resistance" is the trait of a transgenic trehalose-producing plant to sustain prolonged periods of time receiving less water than a wild-type (nontransgenic) plant would normally require or without being watered, and without showing the same degree of wilting of its leaves or other characteristics of dessication that appear in a wild-type plant grown under the same conditions.

"Gene" as used herein comprises a nucleotide sequence optionally operably linked to DNA sequences preceding or following the nucleotide sequence. The nucleotide sequence is typically transcribable into RNA, such as e.g. mRNA (sense RNA or antisense RNA), rRNA, tRNA or snRNA. A nucleotide sequence in a gene optionally comprises a coding sequence, which can be translated into a polypeptide. Examples of DNA sequences preceding or following the nucleotide sequence are 5' and 3' untranslated sequences, termination signals and ribosome binding sites (rbs), or portions thereof. Further elements that may also be present in a gene are, for example, introns.

"Expression cassette" as used herein means a DNA construct designed so that a nucleotide sequence inserted herein can be transcribed and, optionally translated, in an appropriate host cell. The expression cassette typically comprises regulatory elements, such as a promoter capable of directing expression of the nucleotide sequence operably linked to the nucleotide sequence, which is itself optionally operably linked to 3' sequences, such as 3' regulatory sequences or termination signals. The expression cassette also may comprises sequences required for proper translation of a coding sequence comprised in the nucleotide sequence. The nucleotide sequence usually comprises the coding sequence of a protein but may also code for a functional RNA of interest, for example antisense RNA or a nontranslated RNA that, in the sense or antisense direction, inhibits expression of a particular gene, e.g., antisense RNA. The expression cassette comprising the nucleotide sequence of interest may be polycistronic, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue or organ or stage of development. A nuclear expression cassette is usually inserted into the nuclear genome of a plant and is capable of directing the expression of a particular nucleotide sequence from the nuclear genome of said plant. A plastid expression cassette is usually inserted in to the plastid genome of a plant and is capable of directing the expression of a particular nucleotide sequence from the plastid genome of said plant, for example a promoter transcribed by a RNA polymerase normally present in plastids, such as a nuclear-encoded polymerase or a plastid-encoded polymerase, or a transactivator-mediated promoter. A plastid expression cassette as described herein may optionally comprise an operon-like polycistronic gene.

"Regulatory elements" refer to DNA sequences involved in the expression of a nucleotide sequence. Regulatory elements comprise a promoter operably linked to the nucleotide sequence of interest, and may also include 5' and 3' untranslated regions (UTR) or termination signals. They also typically encompass sequences required for proper translation of the nucleotide sequence, such as, in the case of expression in plastids, ribosome binding sites (rbs).

"Heterologous" as used herein means "of different natural origin" or represents a nonnatural state. For example, if a host cell is transformed with a nucleotide sequence derived from another organism, particularly from another species, that nucleotide sequence is heterologous with respect to that host cell and also with respect to descendants of the host cell which carry that gene. Similarly, heterologous refers to a nucleotide sequence derived from and inserted into the same natural, original cell type, but which is present in a non-natural state, e.g. a different copy number, or under the control of different regulatory elements. A transforming nucleotide sequence may comprise a heterologous coding sequence, or heterologous regulatory elements. Alternatively, the transforming nucleotide sequence may be completely heterologous or may comprise any possible combination of heterologous and endogenous nucleic acid sequences.

"Expression" refers to the transcription and/or translation of a nucleotide sequence, for example an endogenous gene or a heterolous gene, in a host organism, e.g. microbes or plants. In the case of antisense constructs, for example, expression may refer to the transcription of the antisense DNA only An "operon-like polycistronic gene" comprises two or more genes of interest under control of a single promoter capable of directing the expression of such operon-like polycistronic gene in plant plastids. Every gene in a operon-like polycistronic gene optionally comprises a ribosome binding site (rbs) operably linked to the 5' end of the nucleotide sequence. Preferably each rbs in the operon-like polycistronic gene is different. The operon-like polycistronic gene also typically comprises a 5' UTR operably linked to the 5' end of the rbs of the first gene in the operon-like polycistronic gene and a 3' UTR operably linked to the 3' end of the last gene in the operon-like polycistronic gene. Two genes in a operon-like polycistronic gene may also comprise several nucleic acids which overlap between the two genes.

"Homoplastidic" refers to a plant, plant tissue or plant cell wherein all of the plastids are genetically identical. This is the normal state in a plant when the plastids have not been transformed, mutated, or otherwise genetically altered. In different tissues or stages of development, the plastids may take different forms, e.g., chloroplasts, proplastids, etioplasts, amyloplasts, chromoplasts, and so forth.

"Marker gene": a gene encoding a selectable or screenable trait.

"Inducible Promoter": An "inducible promoter" is a promoter which initiates transcription only when the plant is exposed to some particular external stimulus, as distinguished from constitutive promoters or promoters specific to a specific tissue or organ or stage of development. Particularly preferred for the present invention are chemically-inducible promoters and wound-inducible promoters. Chemically inducible promoters include plant-derived promoters, such as the promoters in the systemic acquired resistance pathway, for example the PR promoters, e.g., the PR-1, PR-2, PR-3, PR-4, and PR-5 promoters, especially the tobacco PR-1a promoter and the *Arabidopsis* PR-1 promoter, which initiate transcription when the plant is exposed to BTH and related chemicals. See U.S. Pat. No. 5,614,395, incorporated herein by reference, and WO 98/03536, incorporated herein by reference. Chemically-inducible promoters also include receptor-mediated systems, e.g., those derived from other organisms, such as steroid-dependent gene expression, copper-dependent gene expression, tetracycline-dependent gene expression, and particularly the expression system utilizing the USP receptor from *Drosophila* mediated by juvenile growth hormone and its agonists, described in EP-A 0 859 851, incorporated herein by reference, as well as systems utilizing combinations of receptors, e.g., as described in EP-A 0 813 604, incorporated herein by reference. Wound inducible promoters include promoters for proteinase inhibitors, e.g., the proteinase inhibitor II promoter from potato, and other plant-derived promoters involved in the wound response pathway, such as promoters for polyphenyl oxidases, LAP and TD. See generally, C. Gatz, "Chemical Control of Gene Expression", Annu. Rev. Plant Physiol. Plant Mol. Biol. (1997) 48: 89–108, the contents of which are incorporated herein by reference.

"Operably linked to/associated with": a DNA sequence, for example comprising a regulatory element, is said to be "operably linked to" or "associated with" a nucleotide sequence if the two sequences are situated such that the DNA sequence affects expression of the nucleotide sequence.

"Phenotypic trait": a detectable property resulting from the expression of one or more genes.

"Plant": A "plant" refers to any plant or part of a plant at any stage of development. In some embodiments of the invention, the plants may be lethally wounded to induce expression or may be induced to express lethal levels of a desired protein, and so the term "plant" as used herein is specifically intended to encompass plants and plant material which have been seriously damaged or killed, as well as viable plants, cuttings, cell or tissue cultures, and seeds. Preferably, plants of the present invention are distinguished in that they are developmentally normal up to the point of induction of the trehalose biosynthetic gene.

"Plant cell": a structural and physiological unit of the plant, comprising a protoplast and a cell wall. The plant cell may be in form of an isolated single cell or a cultured cell, or as a part of higher organized unit such as, for example, a plant tissue, or a plant organ.

"Plant material": refers to leaves, stems, roots, flowers or flower parts, fruits, pollen, pollen tubes, ovules, embryo sacs, egg cells, zygotes, embryos, seeds, plastids, mitochondria, cuttings, cell or tissue cultures, or any other part or product of a plant.

"Progeny" as used herein comprises all the subsequent generations obtained by self-pollination or out-crossing of a plant of the present invention.

"Promoter": a DNA sequence that initiates transcription of an associated DNA sequence. The promoter region may also include elements that act as regulators of gene expression such as activators, enhancers, and/or repressors.

"Protoplast": isolated plant cell where the cell wall has been totally or partially removed.

"Recombinant DNA molecule": a combination of DNA sequences that are joined together using recombinant DNA technology.

"Recombinant DNA technology": procedures used to join together DNA sequences as described, for example, in Sambrook et al., 1989, Cold Spring Harbor, N.Y.: Cold Spring Harbor Laboratory Press.

"Screenable marker gene": a gene whose expression does not confer a selective advantage to a transformed cell, but whose expression makes the transformed cell phenotypically distinct from untransformed cells.

"Selectable marker gene": a gene whose expression in a plant cell gives the cell a selective advantage. The selective advantage possessed by the cells transformed with the selectable marker gene may be due to their ability to grow in the presence of a negative selective agent, such as an antibiotic or a herbicide, compared to the growth of non-transformed cells. The selective advantage possessed by the transformed cells, compared to non-transformed cells, may also be due to their enhanced or novel capacity to utilize an added compound as a nutrient, growth factor or energy source. Selectable marker gene also refers to a gene or a combination of genes whose expression in a plant cell gives the cell both, a negative and a positive selective advantage.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90%, more preferably at least 95%, still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or at http://www-hto.usc.edu/software/seqaln/index.html). The locals program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

The term "substantially similar", when used herein with respect to a protein, means a protein corresponding to a reference protein, wherein the protein has substantially the same structure and function as the reference protein, e.g. where only changes in amino acids not affecting the polypeptide function occur. When used for a protein or an amino acid sequence the percentage of identity between the substantially similar and the reference protein or amino acid sequence desirably is at least 80%, more desirably 85%, preferably at least 90%, more preferably at least 95%, still more preferably at least 99%.

"Transactivator": A "transactivator" is a protein which, by itself or in combination with one or more additional proteins, is capable of causing transcription of a coding region under control of a corresponding transactivator-mediated promoter. Examples of transactivator systems include phage T7 gene 10 promoter, the transcriptional activation of which is dependent upon a specific RNA polymerase such as the phage T7 RNA polymerase. The transactivator is typically an RNA polymerase or DNA binding protein capable of interacting with a particular promoter to initiate transcription, either by activating the promoter directly or by inactivating a repressor gene, e.g., by suppressing expression or accumulation of a repressor protein. The DNA binding protein may be a chimeric protein comprising a binding region (e.g., the GAL4 binding region) linked to an appropriate transcriptional activator domain. Some transactivator systems may have multiple transactivators, for example promoters which require not only a polymerase but also a specific subunit (sigma factor) for promotor recognition, DNA binding, or transcriptional activation. The transactivator is preferably heterologous with respect to the plant.

"Transformation:" Introduction of a nucleotide sequence into a cell. In particular, the stable integration of a DNA molecule into the genome of an organism of interest.

"Trehalose biosynthetic enzymes" are polypeptides involved in the biosynthesis of trehalose from glucose, e.g., as described herein, particularly trehalose-6-phosphate synthase which catalyses the condensation of UDP-glucose and glucose-6-phosphate into trehalose-6-phosphate or trehalose-6-phosphate phosphatase which phosphorylates trehalose-6-phosphate to trehalose. The nucleotide sequences encoding the trehalose biosynthetic enzymes are comprised in trehalose biosynthetic genes.

"Trehalose" is a D-glucopyranosyl-[1,1]-D-glucopyranoside. The prefered form of trehalose in the present invention is a,a-trehalose (a-D-glucopyranosyl-[1,1]-a-D-glucopyranoside).

DETAILED DESCRIPTION OF THE INVENTION

The present invention also encompasses cells comprising a DNA molecule of the present invention, wherein the DNA molecule is not in its natural cellular environment. In a preferred embodiment, such cells are plant cells. In another prefered embodiment, a DNA molecule of the present invention is expressible in such cells and is comprised in an expression cassette which allow their expression in such cells. In a preferred embodiment, the expression cassette is stably integrated into the DNA of such host cell. In another preferred embodiment, the expression cassette is comprised in a vector, which is capable of replication in the cell and remains in the cell as an extrachromosomal molecule.

In the present invention, trehalose biosynthetic genes from *E. coli* are preferably used, but trehalose biosynthetic genes from other organisms including but not limited to yeast, other lower organisms or higher organisms, such as plants, are suitable. For example, the yeast TPS1, TSL1 or TSL2 genes (U.S. Pat. No. 5,792,921), the *Arabidopsis* trehalose synthase gene (TPS1, accession number Y08568, Blazquez et al. *Plant J* (1998) 13:685–9), *Arabidopsis* trehalose phosphate phosphatases (Vogel et al. *Plant J* (1998) 13:673–83) or a *Selaginella lepidophylla* gene (accession number U96736).

The present invention also encompasses a plant comprising the plant cells described above. In a further embodiment, the DNA molecules of the present invention are expressible in the plant, and expression of any one of the DNA molecules of the present invention or of a functional portion or derivative thereof in transgenic plants confers production of trehalose and leads to drought-resistance, increased storage properties of the harvested plant, improved food quality, e.g. shelf-life of fruits or vegetables derived from said plant, improved longevity of flowers, stabilization of proteins expressed in said plant, preferably transgenic proteins, or high levels of trehalose useful for industrial production, and other characteristics as described herein. The present invention therefore also encompasses transgenic plants which express trehalose due to the expression of any one of the DNA molecules of the present invention or of a functional portion or derivative thereof.

Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidopsis thaliana*, and woody plants such as coniferous and deciduous trees.

Preferred are monocot plants selected from the group consisting of maize, wheat barley, rye, sorghum, and rice. Further preferred are dicot plants selected from the group consisting of chicory, lettuce, cabbage, cauliflower, broccoli, pepper, squash, pumpkin, zucchini, melon, soybean, tomato, sugarcane, sugarbeet, sunflower, rapeseed, cotton, and alfalfa. Preferred groups of plants are plants producing vegetable, fruits and flowers.

Once a desired nucleotide sequence has been transformed into a particular plant species, it may be propagated in that species or moved into other varieties of the same species, particularly including commercial varieties, using traditional breeding techniques, e.g. by recurrent selection breeding, like backcrossing. In this case, the recurrent parent in which the desired transgene is to be introgressed is first crossed to the non-recurrent parent that carries the transgene in question. The progeny of this cross is then mated back to the recurrent parent followed by selection in the resultant progeny for the transgene to be transferred from the non-recurrent parent. After three, preferably four, more preferably five or more generations of backcrosses with the recurrent parent with selection for the transgene, the progeny will be heterozygous for the transgene being transferred, but will be like the recurrent parent for most or almost all other genes.

For their expression in transgenic plants, the DNA molecules may require modification and optimization, particularly when the DNA molecules are of prokaryotic origin. It is known in the art that all organisms have specific preferences for codon usage, and the codons in the nucleotide sequence comprised in the DNA molecules of the present invention can be changed to conform with specific plant preferences, while maintaining the amino acids encoded thereby. Furthermore, high expression in plants is best achieved from coding sequences which have at least 35% GC content, and preferably more than 45%. Nucleotide sequences which have low GC contents may express poorly due to the existence of ATTTA motifs which may destabilize messages, and AATAAA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). In addition, the nucleotide sequences are screened for the existence of illegitimate splice sites which cause message truncation. All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol), and WO 93/07278 (to Ciba-Geigy).

For efficient initiation of translation, sequences adjacent to the initiating methionine may require modification. For example, they can be modified by the inclusion of sequences known to be effective in plants. Joshi has suggested an appropriate consensus for plants (NAR 15: 6643–6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequence, up to and including the ATG (whilst leaving the second amino acid unmodified), or alternatively up to and including the GTC subsequent to the ATG (with the possibility of modifying the second amino acid of the transgene).

In transgenic plants, the DNA molecules of the present invention, for example trehalose biosynthetic genes or genes encoding a transactivator, are driven by a promoter shown to be functional in plants. The choice of promoter will vary depending on the temporal and spatial requirements for expression, and also depending on the target species. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the DNA molecules in the desired cell.

Preferred promoters which are expressed constitutively include the CaMV 35S and 19S promoters, promoters from genes encoding actin or ubiquitin, and promoters derived from *Agrobacterium*, for example synthetic promoters as described in PCT/US94/12946. The DNA molecules of this invention, however, are preferably expressed under the regulation of promoters which are chemically regulated. This enables the trehalose to be synthesized only when the crop plants are treated with the inducing chemicals, thereby avoiding developmental abnormalities in the young plants. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A second preferred category of inducible promoters is that which is wound inducible, permitting expression of the trehalose biosynthetic enzymes when the plant is injured, for example at harvest, or in silage or other processing. Numerous promoters have been described which are expressed at wound sites. Preferred promoters of this kind include those described by Stanford et al. Mol. Gen. Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12: 579–589 (1989)). A preferred promoter for root specific expression is that described by de Framond (FEBS 290: 103–106 (1991); EP 0 452 269 to Ciba-Geigy) and a further preferred root-specific promoter is that from the T-1 gene provided by this invention. A preferred stem specific promoter is that described in U.S. Pat. No. 5,625,136 (to Ciba-Geigy) and which drives expression of the maize trpA gene.

In addition to the selection of a suitable promoter, constructions for expression of the protein in plants optionally require an appropriate transcription terminator to be attached downstream of the heterologous nucleotide sequence. Several such terminators are available and known in the art (e.g. tm1 from CaMV, E9 from rbcS). Any available terminator known to function in plants can be used in the context of this invention. Numerous other sequences can be incorporated into expression cassettes for the DNA molecules of this invention. These include sequences which have been shown to enhance expression such as intron sequences (e.g. from Adh 1 and bronze1) and viral leader sequences (e.g. from TMV, MCMV and AMV).

It may be preferable to target expression of the DNA molecules to different cellular localizations in the plant. In some cases, localization in the cytosol may be desirable, whereas in other cases, localization in some subcellular organelle may be prefered. Subcellular localization of transgene encoded enzymes can be undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. A preferred class of targeting sequences are the vacuole targeting sequences, e.g., as found on plant chitinases and proteases.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093–1096 (1986)). For both direct gene transfer and *Agrobacterium*-mediated transfer, transformation is usually (but not necessarily) undertaken with a selectable marker which may provide resistance to an antibiotic (kanamycin, hygromycin or methatrexate) or a herbicide (basta). The choice of selectable marker is not, however, critical to the invention.

In another preferred embodiment, the DNA molecules of this invention are directly transformed into the plastid genome. Plastid transformation technology is described extensively in U.S. Pat. Nos. 5,451,513, 5,545,817, 5,545,818 and 5,576,198; in PCT application nos. WO 95/16783 and WO 97/32977; and in McBride et al., Proc. Natl. Acad. Sci. USA 91: 7301–7305 (1994), all of which are incorporated herein by reference. Plastid transformation via biolistics was achieved initially in the unicellular green alga *Chlamydomonas reinhardtii* (Boynton et al. (1988) Science 240: 1534–1537, incorporated herein by reference) and this approach, using selection for cis-acting antibiotic resistance loci (spectinomycin/streptomycin resistance) or complementation of non-photosynthetic mutant phenotypes, was soon extended to *Nicotiana tabacum* (Svab et al. (1990) Proc. Natl. Acad. Sci. USA. 87: 8526–8530, incorporated herein by reference).

The basic technique for tobacco plastid transformation involves the particle bombardment of leaf or callus tissue or PEG-mediated uptake of plasmid DNA in protoplasts with regions of cloned plastid DNA flanking a selectable antibiotic resistance marker. The 1 to 1.5 kb flanking regions, termed targeting sequences, facilitate homologous recombination with the plastid genome and thus allow the replacement or modification of specific regions of the 156 kb tobacco plastid genome. Initially, point mutations in the plastid 16S rDNA and rps12 genes conferring resistance to spectinomycin and/or streptomycin were utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45, incorporated herein by reference). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P., EMBO J. 12: 601–606 (1993), incorporated herein by reference). Substantial increases in transformation frequency were obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913–917, incorporated herein by reference). Previously, this marker had been used successfully for high-frequency transformation of the plastid genome of the green alga *Chlamy-*

*domonas reinhardtii* (Goldschmidt-Clermont, M. (1991) Nucl. Acids Res. 19, 4083–4089, incorporated herein by reference). Recently, plastid transformation of protoplasts from tobacco and the moss *Physcomitrella patens* has been attained using polyethylene glycol (PEG) mediated DNA uptake (O'Neill et al. (1993) *Plant J.* 3: 729–738; Koop et al. (1996) *Planta* 199: 193–201, both of which are incorporated herein by reference). Both particle bombardment and protoplast transformation are appropriate in the context of the present invention.

A DNA molecule of the present invention is inserted into a plastid expression cassette comprising a promoter capable of expressing the DNA molecule in plant plastids. A preferred promoter capable of expression in a plant plastid is a promoter isolated from the 5' flanking region upstream of the coding region of a plastid gene, which may come from the same or a different species, and the native product of which is typically found in a majority of plastid types including those present in non-green tissues. Gene expression in plastids differs from nuclear gene expression and is related to gene expression in prokaryotes (described in Stern et al. (1997) *Trends in Plant Sciences* 2: 308–315, incorporated herein by reference). Plastid promoters generally contain the −35 and −10 elements typical of prokaryotic promoters and some plastid promoters are recognized by a *E. coli*-like RNA polymerase mostly encoded in the plastid genome and are called PEP (plastid-encoded RNA polymerase) promoters while other plastid promoters are recognized by a nuclear-encoded RNA polymerase (NEP promoters). Both types of plastid promoters are suitable for the present invention. Examples of plastid promoters are promoters of clpP genes, such as the tobacco clpP gene promoter (WO 97/06250, incorporated herein by reference) and the *Arabidopsis* clpP gene promoter (U.S. application Ser. No. 09/038,878, incorporated herein by reference). Another promoter that is capable of expressing a DNA molecule in plant plastids comes from the regulatory region of the plastid 16S ribosomal RNA operon (Harris et al., *Microbiol. Rev.* 58:700–754 (1994), Shinozaki et al., *EMBO J.* 5:2043–2049 (1986), both of which are incorporated herein by reference). Other examples of promoters that are capable of expressing a DNA molecule in plant plastids are a psbA promoter or a rbcL promoter. A plastid expression cassette also preferably further comprises a plastid gene 3' untranslated sequence (3'UTR) operatively linked to a DNA molecule of the present invention. The role of untranslated sequences is preferably to direct the 3' processing of the transcribed RNA rather than termination of transcription. Preferably, the 3' UTR is a plastid rps16 gene 3' untranslated sequence or the *Arabidopsis* plastid psbA gene 3' untranslated sequence. In a further preferred embodiment, a plastid expression cassette comprises a poly-G tract instead of a 3' untranslated sequence. A plastid expression cassette also preferably further comprises a 5' untranslated sequence (5'UTR) functional in plant plastids operatively linked to a DNA molecule of the present invention.

A plastid expression cassette is comprised in a plastid transformation vector, which preferably further comprises flanking regions for integration into the plastid genome by homologous recombination. The plastid transformation vector may optionally comprise at least one plastid origin of replication. The present invention also encompasses a plant plastid transformed with such a plastid transformation vector, wherein the DNA molecule is expressible in the plant plastid. The invention also encompasses a plant or plant cell, including the progeny thereof, comprising this plant plastid.

In a preferred embodiment, the plant or plant cell, including the progeny thereof, is homoplasmic for transgenic plastids.

Other promoters that are capable of expressing a DNA molecule in plant plastids are transactivator-regulated promoters, preferably heterologous with respect to the plant or to the subcellular organelle or component of the plant cell in which expression is effected. In these cases, the DNA molecule encoding the transactivator is inserted into an appropriate nuclear expression cassette which is transformed into the plant nuclear DNA. The transactivator is targeted to plastids using a plastid transit peptide. The transactivator and the transactivator-driven DNA molecule are brought together either by crossing to a selected plastid-transformed line a transgenic line containing a DNA molecule encoding the transactivator supplemented with a plastid-targeting sequence and operably linked to a nuclear promoter, or by directly transforming a plastid transformation vector containing the desired DNA molecule into a transgenic line containing a DNA molecule encoding the transactivator supplemented with a plastid-targeting sequence and operably linked to a nuclear promoter. If the nuclear promoter is an inducible promoter, in particular a chemically inducible promoter, expression of the DNA molecule in the plastids of plants is activated by foliar application of a chemical inducer. Such inducible transactivator-mediated plastid expression system is preferably tightly regulatable, with no detectable expression prior to induction and exceptionally high expression and accumulation of protein following induction. A preferred transactivator is for example viral RNA polymerase. Preferred promoters of this type are promoters recognized by a single sub-unit RNA polymerase, such as the T7 gene 10 promoter, which is recognized by the bacteriophage T7 DNA-dependent RNA polymerase. The gene encoding the T7 polymerase is preferably transformed into the nuclear genome and the T7 polymerase is targeted to the plastids using a plastid transit peptide. Promoters suitable for nuclear expression of a gene, for example a gene encoding a viral RNA polymerase such as the T7 polymerase, are described infra or supra. Expression of the DNA molecules in plastids can be constitutive or can be inducible Expression of the DNA molecules in the plastids can be also organ- or tissue-specific. These different embodiment are extensively described in WO 98/11235, incorporated herein by reference. Thus, in one aspect, the present invention has coupled expression in the nuclear genome of a choroplast-targeted phage T7 RNA polymerase under control of the chemically inducible PR-1a promoter (U.S. Pat. No. 5,614,395 incorporated by reference) of tobacco to a chloroplast reporter transgene regulated by T7 gene 10 promoter/terminator sequences. For example, when plastid transformants homoplasmic for the maternally inherited trehalose biosynthetis genes are pollinated by lines expressing the T7 polymerase in the nucleus, F1 plants are obtained that carry both transgene constructs but do not express them. Synthesis of large amounts of enzymatically active protein is triggered in plastids of these plants only after foliar application of the PR-1a inducer compound benzo(1,2,3)thiadiazole-7-carbothioic acid S-methyl ester (BTH).

In a preferred embodiment, two or more genes, e.g. trehalose biosynthetic genes, are transcribed from the plastid genome from a single promoter in an operon-like polycistronic gene. In a preferred embodiment, the operon-like polycistronic gene comprises an intervening DNA sequence between two genes in the operon-like polycistronic gene. In a preferred embodiment, the DNA sequence is not present in the plastid genome to avoid homologous recombination with plastid sequences. In another preferred embodiment, the DNA sequence is derived from the 5' untranslated (UTR) region of a non-eukaryotic gene, preferably from a viral 5'UTR, preferably from a 5'UTR derived from a bacterial phage, such as a T7, T3 or SP6 phage. In a preferred embodiment, the DNA sequence is modified to prevent the formation of RNA secondary structures in a RNA transcript of the operon-like polycistronic gene, e.g. between the DNA sequence and the rbs of the downstream gene. Such secondary structures would inhibit or repress the expression of the downstream gene, particularly the initiation of its translation. Such RNA secondary structures are predicted by determining their melting temperatures using computer models and programs such a the "mfold" program version 3 (by Zuker and Turner, Washington University School of Medicine, St-Louis, Mo.) and other methods well known to one skilled in the art. Such a DNA sequence is exemplified below.

The presence of the intervening DNA sequence in the operon-like polycistronic gene increases the accessibility of the rbs of the downstream gene, thus resulting in higher rates of expression. Such strategy is applicable to any two or more genes to be transcribed from the plastid genome from a single promoter in an operon-like chimeric gene. Such genes can be part of a metabolic pathway, or are genes encoding input or output traits. Example of metabolic pathways are e.g. sugar biosynthetic pathways, such as trehalose or fructans.

In a further embodiment, the DNA molecules of the present invention are modified by incorporation of random mutations in a technique known as in-vitro recombination or DNA shuffling. This technique is described in Stemmer et al., Nature 370: 389–391 (1994) and U.S. Pat. No. 5,605,793 incorporated herein by reference. Millions of mutant copies of the nucleotide sequences are produced based on the original nucleotide sequence described herein and variants with improved properties, such as increased activity or altered specificity are recovered. The method encompasses forming a mutagenized double-stranded polynucleotide from a template double-stranded polynucleotide comprising the nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized doubles-tranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another embodiment, the size of the double-stranded random fragments is from about 5 bp to 5 kb. In a further embodiment, the fourth step of the method comprises repeating the second and the third steps for at least 10 cycles.

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptll gene which confers resistance to kanamycin and related antibiotics (Messing & Vierra, Gene 19: 259–268 (1982); Bevan et al., Nature 304:184–187 (1983)), the bar gene which confers resistance to the herbicide phosphinothricin (White et al., Nucl! Acids Res 18: 1062 (1990), Spencer et al. Theor Appl Genet 79: 625–631(1990)), the hpt gene which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)).

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below the construction of two typical vectors is described.

Construction of pCIB200 and pCIB2001: The binary vectors pCIB200 and pCIB2001 are used for the construction of recombinant vectors for use with *Agrobacterium* and was constructed in the following manner. pTJS75kan was created by NarI digestion of pTJS75 (Schmidhauser & Helinski, J Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et al., Plant Molecular Biology 14: 266–276 (1990)). XhoI linkers were ligated to the EcoRV fragment of pCIB7 which contains the left and right T-DNA borders, a plant selectable nos/nptll chimeric gene and the pUC polylinker (Rothstein et al., Gene 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof: The binary vector pCIB10 contains a gene encoding kanamycin resistance for selection in plants, T-DNA right and left border sequences and incorporates sequences from the wide host-range plasmid pRK252 allowing it to replicate in both *E. coli* and *Agrobacterium*. Its construction is described by Rothstein et al. (Gene 53: 153–161 (1987)). Various derivatives of pCIB10 have been constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on *Agrobacterium* include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064: pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from *Streptomyces viridochromogenes* was excised and inserted into the HpaI site of pCIB3060 (Thompson et al. EMBO J 6: 2519–2523 (1987)). This generated pCIB3064 which comprises the bar gene under the control of the CaMV 35S promoter and terminator for herbicide selection, a gene fro ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOG19 and pSOG35: pSOG35 is a transformation vector which utilizes the *E. coli* gene dihydrofolate reductase (DHFR) as a selectable marker conferring resistance to methotrexate. PCR was used to amplify the 35S promoter (~800 bp), intron 6 from the maize AdH1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Gene sequences intended for expression in transgenic plants are firstly assembled in expression cassettes behind a suitable promoter and upstream of a suitable transcription terminator. These expression cassettes can then be easily transferred to the plant transformation vectors described above.

The selection of promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of biosynthesis of the enzyme. Alternatively, the selected promoter may drive expression of the gene under a light-induced or other temporally regulated promoter. A further (and preferred) alternative is that the selected promoter be inducible by an external stimulus, e.g., application of a specific chemical inducer or wounding. This would provide the possibility of inducing trehalose biosynthetic gene transcription only when desired.

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase terminator, the pea rbcS E9 terminator. These can be used in both monocotyledons and dicotyledons.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develep 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15; 65–79 (1990)).

Various mechanisms for targeting gene products are known to exist in plants and the sequences controlling the functioning of these mechanisms have been characterized in some detail. For example, the targeting of gene products to the chloroplast is controlled by a signal sequence found at the aminoterminal end of various proteins and which is cleaved during chloroplast import yielding the mature protein (e.g. Comai et al. J. Biol. Chem. 263: 15104–15109 (1988)). These signal sequences can be fused to heterologous gene products to effect the import of heterologous products into the chloroplast (van den Broeck et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al. (Proc. Natl. Acad. Sci. USA 82: 6512–6516 (1985)).

In addition, sequences have been characterized which cause the targeting of gene products to other cell compartments. Aminoterminal sequences are responsible for targeting to the ER, the apoplast, and extracellular secretion from aleurone cells (Koehler & Ho, Plant Cell 2: 769–783 (1990)). Additionally, aminoterminal sequences in conjunction with carboxyterminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the aminoterminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gen. Genet. 205: 446–453 (1986)). These construction techniques are well known in the art and are equally applicable to mitochondria and peroxisomes. The choice of targeting which may be required for trehalose biosynthetic genes will depend on the cellular localization of the precursor required as the starting point for a given pathway. This will usually be cytosolic or chloroplastic, although it may is some cases be mitochondrial or peroxisomal.

The above-described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

The present invention encompasses the expression of trehalose biosynthetic genes under the regulation of any promoter that is expressible in plants, regardless of the origin of the promoter.

Furthermore, the invention encompasses the use of any plant-expressible promoter in conjunction with any further sequences required or selected for the expression of the trehalose biosynthetic gene. Such sequences include, but are not restricted to, transcriptional terminators, extraneous sequences to enhance expression (such as introns [e.g. Adh intron 1], viral sequences [e. g. TMV-Ω]), and sequences intended for the targeting of the gene product to specific organelles and cell compartments.

Suitable plant-expressible promoters are those that are expressed constitutively such as the CaMV 35S promoter, the actin promoter or the ubiquitin promoter.

Construction of the plasmid pCGN1761 containing the "double" 35S promoter is described in the published patent application EP 0 392 225 (example 23). pCGN1761 contains the "double" 35S promoter and the tml transcriptional terminator with a unique EcoRI site between the promoter and the terminator and has a pUC-type backbone. A derivative of pCGN1761 was constructed which has a modified polylinker which includes NotI and XhoI sites in addition to the existing EcoRI site. This derivative was designated pCGN1761ENX. pCGN1761ENX is useful for the cloning of cDNA sequences or gene sequences (including microbial ORF sequences) within its polylinker for the purposes of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglII sites 3' to the terminator for transfer to transformation vectors such as those described above. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter.

For any of the constructions described in this section, modifications around the cloning sites can be made by the introduction of sequences which may enhance translation. This is particularly useful when genes derived from microorganisms are to be introduced into plant expression cassettes as these genes may not contain sequences adjacent to their initiating methionine which may be suitable for the initiation of translation in plants. In cases where genes derived from microorganisms are to be cloned into plant expression cassettes at their ATG it may be useful to modify the site of their insertion to optimize their expression. Modification of pCGN1761 ENX by optimization of the translational initiation site is described by way of example to incorporate one of several optimized sequences for plant expression (e.g. Joshi, supra).

Further plant-expressible promoters that can be suitably used within the scope of the present invention are chemically regulatable promoters such as those described hereinafter. For example, this section describes the replacement of the double 35S promoter in pCGN1761ENX with any promoter of choice; by way of example, the chemically regulatable PR-1a promoter is described in U.S. Pat. No. 5,614,395, which is hereby incorporated by reference in its entirety, and the chemically regulatable *Arabidopsis* PR-1 promoter is described in U.S. Provisional Application No. 60/027,228, incorporated herein by reference. The promoter of choice is preferably excised from its source by restriction enzymes, but can alternatively be PCR-amplified using primers which carry appropriate terminal restriction sites. Should PCR-amplification be undertaken, then the promoter should be resequenced to check for amplification errors after the cloning of the amplified promoter in the target vector. The chemically regulatable tobacco PR-1a promoter is cleaved from plasmid pCIB1004 (see EP 0 332 104, example 21 for construction) and transferred to plasmid pCGN1761ENX. pCIB1004 is cleaved with NcoI and the resultant 3' overhang of the linearized fragment is rendered blunt by treatment with T4 DNA polymerase. The fragment is then cleaved with HindIII and the resultant PR-1a promoter containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tmI terminator and an intervening polylinker with unique EcoRI and NotI sites. Selected trehalose biosynthetic genes can be inserted into this vector, and the fusion products (i.e. promoter-gene-terminator) can subsequently be transferred to any selected transformation vector, including those described in this application.

Various chemical regulators may be employed to induce expression of the trehalose biosynthetic coding sequence in the plants transformed according to the present invention. In the context of the instant disclosure, "chemical regulators" include chemicals known to be inducers for the PR-1a promoter in plants, or close derivatives thereof. A preferred group of regulators for the chemically inducible trehalose biosynthetic genes of this invention is based on the benzo-1,2,3-thiadiazole (BTH) structure and includes, but is not limited to, the following types of compounds: benzo-1,2,3-thiadiazolecarboxylic acid, benzo-1,2,3-thiadiazolethiocarboxylic acid, cyanobenzo-1,2,3-thiadiazole, benzo-1,2,3-thiadiazolecarboxylic acid amide, benzo-1,2,3-thiadiazolecarboxylic acid hydrazide, benzo-1,2,3-thiadiazole-7-carboxylic acid, benzo-1,2,3-thiadiazole-7-thiocarboxylic acid, 7-cyanobenzo-1,2,3-thiadiazole, benzo-1,2,3-thiadiazole-7-carboxylic acid amide, benzo-1,2,3-thiadiazole-7-carboxylic acid hydrazide, alkyl benzo-1,2,3-thiadiazolecarboxylate in which the alkyl group contains one to six carbon atoms, methyl benzo-1,2,3-thiadiazole-7-carboxylate, n-propyl benzo-1,2,3-thiadiazole-7-carboxylate, benzyl benzo-1,2,3-thiadiazole-7-carboxylate, benzo-1,2,3-thiadiazole-7-carboxylic acid sec-butylhydrazide, and suitable derivatives thereof. Other chemical inducers may include, for example, benzoic acid, salicylic acid (SA), polyacrylic acid and substituted derivatives thereof; suitable substituents include lower alkyl, lower alkoxy, lower alkylthio, and halogen. Still another group of regulators for the chemically inducible DNA sequences of this invention is based on the pyridine carboxylic acid structure, such as the isonicotinic acid structure and preferably the haloisonicotinic acid structure. Preferred are dichloroisonicotinic acids and derivatives thereof, for example the lower alkyl esters. Suitable regulators of this class of compounds are, for example, 2,6-dichloroisonicotinic acid (INA), and the lower alkyl esters thereof, especially the methyl ester.

Constitutive Expression can also be achieved by the Actin Promoter. Several isoforms of actin are known to be expressed in most cell types and consequently the actin promoter is a good choice for a constitutive promoter. In particular, the promoter from the rice Act1 gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the Act1promoter have been constructed specifically for use in monocotyledons (McElroy et al. Mol. Gen. Genet. 231: 150–160 (1991)). These incorporate the Act1-intron 1, AdH1 5' flanking sequence and AdH1-intron 1 (from the maize alcohol dehydrogenase gene) and sequence from the CaMV 35S promoter. Vectors showing highest expression were fusions of 35S and the Act1 intron or the Act1 5' flanking sequence and the Act1 intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for the expression of trehalose biosynthetic genes and are particularly suitable for use in monocotyledonous hosts. For example, promoter containing fragments can be removed from the McElroy constructions and used to replace the double 35S promoter in pCGN1761ENX, which is then available for the insertion or specific gene sequences. The fusion genes thus constructed can then be transferred to appropriate transformation vectors. In a separate report the rice Act1 promoter with its first intron has also been found to direct high expression in cultured barley cells (Chibbar et al. Plant Cell Rep. 12: 506–509 (1993)).

Ubiquitin is another gene product known to accumulate in many cell types and its promoter has been cloned from several species for use in transgenic plants (e.g. sunflower—Binet et al. Plant Science 79: 87–94 (1991), maize—Christensen et al. Plant Molec. Biol. 12: 619–632 (1989)) for constitutive expression. The maize ubiquitin promoter has been developed in transgenic monocot systems and its sequence and vectors constructed for monocot transformation are disclosed in the patent publication EP 0 342 926 (to Lubrizol). Further, Taylor et al. (Plant Cell Rep. 12: 491–495 (1993)) describe a vector (pAHC25) which comprises the maize ubiquitin promoter and first intron and its high activity in cell suspensions of numerous monocotyledons when introduced via microprojectile bombardment. The ubiquitin promoter is suitable for the expression of trehalose biosynthetic genes in transgenic plants, especially monocotyledons. Suitable vectors are derivatives of pAHC25 or any of the transformation vectors described in this application, modified by the introduction of the appropriate ubiquitin promoter and/or intron sequences.

Another pattern of expression for the enzymes of the instant invention is root expression. A suitable root promoter is that described by de Framond (FEBS 290: 103–106 (1991)) and also in the published patent application EP 0 452 269 (to Ciba-Geigy). This promoter is transferred to a suitable vector such as pCGN1761ENX for the insertion of a trehalose biosynthetic gene and subsequent transfer of the entire promoter-gene-terminator cassette to a transformation vector of interest.

Wound-inducible promoters may also be suitable for the expression of trehalose biosynthetic genes. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wun1 gene. Xu et al. show that a wound inducible promoter from the dicotyledon potato (pin2) is active in the monocotyledon rice. Further, Rohrmeier & Lehle describe the cloning of the maize Wip1 cDNA which is wound induced and which can be used to isolated the cognate promoter using standard techniques. Similarly, Firek et al. and Warner et al. have described a wound induced gene from the monocotyledon *Asparagus officinalis* which is expressed at local wound and pathogen invasion sites. Using cloning techniques well known in the art, these promoters can be transferred to suitable vectors, fused to the trehalose biosynthetic genes of this invention, and used to express these genes at the sites of plant wounding.

Patent Application WO 93/07278 (to Ciba-Geigy) describes the isolation of the maize trpA gene which is preferentially expressed in pith cells. The gene sequence and promoter extend up to −1726 from the start of transcription are presented. Using standard molecular biological techniques, this promoter or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

Chen & Jagendorf (J. Biol. Chem. 268: 2363–2367 (1993) have described the successful use of a chloroplast transit peptide for import of a heterologous transgene. This peptide used is the transit peptide from the rbcS gene from *Nicotiana plumbaginifolia* (Poulsen et al. Mol. Gen. Genet. 205: 193–200 (1986)). Using the restriction enzymes DraI and SphI, or Tsp509I and SphI the DNA sequence encoding this transit peptide can be excised from plasmid prbcS-8B and manipulated for use with any of the constructions described above. The DraI-SphI fragment extends from −58 relative to the initiating rbcS ATG to, and including, the first amino acid (also a methionine) of the mature peptide immediately after the import cleavage site, whereas the Tsp509I-SphI fragment extends from -8 relative to the initiating rbcS ATG to, and including, the first amino acid of the mature peptide. Thus, these fragments can be appropriately inserted into the polylinker of any chosen expression cassette generating a transcriptional fusion to the untranslated leader of the chosen promoter (e.g. 35S, PR-1a, actin, ubiquitin etc.), whilst enabling the insertion of a trehalose biosynthetic gene in correct fusion downstream of the transit peptide. Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected trehalose biosynthetic gene. Ideally the ATG of the SphI site is maintained and comprises the first ATG of the selected trehalose biosynthetic gene. Chen & Jagendorf provide consensus sequences for ideal cleavage for chloroplast import, and in each case a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al. (Eds.) Methods in Chloroplast Molecular Biology, Elsevier. pp 1081–1091 (1982)) and Wasmann et al. (Mol. Gen. Genet. 205: 446–453 (1986)). Typically the best approach may be to generate fusions using the selected trehalose biosynthetic gene with no modifications at the aminoterminus, and only to incorporate modifications when it is apparent that such fusions are not chloroplast imported at high efficiency, in which case modifications may be made in accordance with the established literature (Chen & Jagendorf; Wasman et al.; Ko & Ko, J. Biol. Chem. 267: 13910–13916 (1992)).

A preferred vector is constructed by transferring the DraI-SphI transit peptide encoding fragment from prbcS-8B to the cloning vector pCGN1761ENX/Sph-. This plasmid is cleaved with EcoRI and the termini rendered blunt by treatment with T4 DNA polymerase. Plasmid prbcS-8B is cleaved with SphI and ligated to an annealed molecular adaptor. The resultant product is 5'-terminally phosphorylated by treatment with T4 kinase. Subsequent cleavage with DraI releases the transit peptide encoding fragment which is ligated into the blunt-end ex-EcoRI sites of the modified vector described above. Clones oriented with the 5' end of the insert adjacent to the 3' end of the 35S promoter are identified by sequencing. These clones carry a DNA fusion of the 35S leader sequence to the rbcS-8A promoter-transit peptide sequence extending from −58 relative to the rbcS ATG to the ATG of the mature protein, and including at that position a unique SphI site, and a newly created EcoRI site, as well as the existing NotI and XhoI sites of pCGN1761ENX. This new vector is designated pCGN1761/CT. DNA sequences are transferred to pCGN1761/CT in frame by amplification using PCR techniques and incorporation of an SphI, NSphI, or NlaIII site at the amplified ATG, which following restriction enzyme cleavage with the appropriate enzyme is ligated into SphI-cleaved pCGN1761/CT. To facilitate construction, it may be required to change the second amino acid of cloned gene, however, in almost all cases the use of PCR together with standard site directed mutagenesis will enable the construction of any desired sequence around the cleavage site and first methionine of the mature protein.

A further preferred vector is constructed by replacing the double 35S promoter of pCGN1761 ENX with the BamHI-SphI fragment of prbcS-8A which contains the full-length light regulated rbcS-8A promoter from −1038 (relative to the transcriptional start site) up to the first methionine of the mature protein. The modified pCGN1761 with the destroyed SphI site is cleaved with PstI and EcoRI and treated with T4 DNA polymerase to render termini blunt. prbcS-8A is cleaved SphI and ligated to the annealed molecular adaptor of the sequence described above. The resultant product is 5'-terminally phosphorylated by treatment with T4 kinase. Subsequent cleavage with BamHI releases the promoter-transit peptide containing fragment which is treated with T4 DNA polymerase to render the BamHI terminus blunt. The promoter-transit peptide fragment thus generated is cloned into the prepared pCGN1761ENX vector, generating a construction comprising the rbcS-8A promoter and transit peptide with an SphI site located at the cleavage site for insertion of heterologous genes. Further, downstream of the SphI site there are EcoRI (re-created), NotI, and XhoI cloning sites. This construction is designated pCGN1761rbcS/CT.

Similar manipulations can be undertaken to utilize other GS2 chloroplast transit peptide encoding sequences from other sources (monocotyledonous and dicotyledonous) and from other genes. In addition, similar procedures can be followed to achieve targeting to other subcellular compartments such as mitochondria.

Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton [1313]), EP 0 249 432 (tomato, to Calgene), WO 87/07299 (*Brassica*, to Calgene), U.S. Pat. No. 4,795,855 (poplar)). *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to *Agrobacterium* is accomplished by a triparental mating procedure using *E. coli* carrying the recombinant binary vector, a helper *E coli* strain which carries a plasmid such as pRK2013 and which is able to mobilize the recombinant binary vector to the target *Agrobacterium* strain. Alternatively, the recombinant binary vector can be transferred to Agrobacterium by DNA transformation (Höfgen & Willmitzer, Nucl. Acids Res. 16: 9877(1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435 ([1280/1281] to Ciba-Geigy), EP 0 392 225 (to Ciba-Geigy) and WO 93/07278 (to Ciba-Geigy) describe techniques for the preparation of callus and protoplasts from an 6lite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, application WO 93/07278 (to Ciba-Geigy) and Koziel et al. (Biotechnology 11: 194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. patent application Ser. No. 08/147,161 describes methods for wheat transformation and is hereby incorporated by reference.

The invention will be further described by reference to the following detailed examples. These examples are provided for purposes of illustration only, and are not intended to be limiting unless otherwise specified.

EXAMPLES

A. Expression of the Trehalose-6-phosphate Synthase and Trehalose-6-phosphate Phosphatase Genes in the Plant Cytosol

Example 1

Preparation of a Chimeric Gene Containing the *E. coli* Trehalose-6-phosphate Synthase Gene Fused to the Tobacco PR-1a Promoter Plasmid pCGN4467 containing the coding sequence of the *E coli* trehalose-6-phosphate synthase gene (OtsA, Kaasen et al. (1994) Gene 145 (1), 9–15, EMBL/UGenbank accession number X69160) under the control of a double 35S promoter and fused to the tml3' polyadenylation signals (pCGN4467 is a derivative of pCGN1761, EP 0392225) is used as template for PCR with a left-to-right "topstrand" primer including the ATG preceded by a GCC codon and followed by a newly added GCA codon, thus creating a NcoI restriction site at the ATG, and the first 24 bases of the OtsA gene (primer TREA+: GTC AGC CAT GGC MG TCG TTT AGT CGT AGT ATC TAA C, SEQ ID No:1) and a right-to-left "bottomstrand" primer homologous to positions 392 to 416 downstream of the new ATG (primer TREA-: GCA MT GGC MC AGG TGA TAA TCG, SEQ ID No:2). This PCR reaction is undertaken with AmpliTaq DNA polymerase according to the manufacturer's recommendations (Perkin Elmer/Roche, Branchburg, N.J.) for five cycles at 94° C. (30 s), 40° C. (60 s), and 72° C. (30 s) followed by 25 cycles at 94° C. (30 s), 55° C. (60 s) and 72°C. (30 s) and this generated a product of 423 bp containing a NcoI site at its left end and a BamHI site at its right end. The fragment is gel purified using standard procedures, cleaved with NcoI and BamHI (all restriction enzymes are purchased from Promega, Madison, Wis.) and ligated into the NcoI and BamHI sites of pUC21 which is a pUC derivative containing a polylinker with the following restriction sites: SpeI/StuI/XhoI/BglII/ClAI/NsiI/SphI/NcoI/KpnI/XmaI/SmaI/SacI/EcoRI/BstIBI/HindIII/PstI/MluI/SalI/AatII/NdeI/BamHI/EcoRV/NotI/EagI/XbaI/SpeI to obtain pUCOTSA.

Plasmid pUCOTSA is then digested with SpeI and BamHI, the 400bp fragment containing the 5' end of the OtsA gene is gel purified and ligated with pCGN4467 that had previously been digested with XbaI and BamHI, to obtain pCGNOTSA containing the entire OtsA gene. Plasmid pCGNOTSA is digested with NcoI and SacI, the 1.4 kb long fragment containing the OtsA gene is gel purified and ligated into the NcoI and SacI sites of pJG203 between a 903 bp long tobacco PR-1a promoter and the nos gene termination signals (Uknes et al. (1993), The Plant Cell 5,159–169). Plasmid pJG203 is a derivative of pBSGusl.2 (Uknes et al. (1993), The Plant Cell 5,159–169), comprising a 903 bp long tobacco PR-1a promoter fused to the GUS gene and nos polyadenylation signals. In pJG203, the second SacI site at the end of the nos polyadenylation signals has been removed by partial digestion with SacI, filling-in of the protruding ends and religation. Plasmid pPR10TSA containing the OtsA gene fused to the tobacco PR-1a promoter is thus obtained.

Example 2

Preparation of a Chimeric Gene Containing the *E. coli* Trehalose-6-phosphate Phosphatase Gene Fused to the Tobacco PR-1a Promoter Plasmid pCGN4452 containing the coding sequence of the *E. coli* trehalose-6-phosphate phosphatase gene (OtsB, Kaasen et al. (1994) Gene 145 (1), 9–15, EMBL-Genbank accession number X69160) under the control of a double 35S promoter and fused to the tml3' polyadenylation signals (pCGN4452 is a derivative of pCGN1761, EP0392225) is used as template for PCR with a left-to-right "topstrand" primer including a newly created ATG codon before the original GTG start codon, preceded by a GCC codon, thus creating a NcoI restriction site at the ATG, and the first 23 bases of the OtsA gene (primer TREB+: GTC AGC CAT GGT GAC AGA ACC GTT MC CGA MC, SEQ ID No:3) and a right-to-left "bottomstrand" primer homologous to positions 181 to 205 downstream of the new ATG (primer TREB-; GTG CGT CAA GCT CCA CCA TTG AGC, SEQ ID No:4). This PCR reaction is undertaken with AmpliTaq DNA polymerase according to the manufacturer's recommendations (Perkin Elmer/Roche, Branchburg, N.J.) for five cycles at 94° C. (30 s), 4° C. (60 s), and 72°C. (30 s) followed by 25 cycles at 94° C. (30 s), 55° C. (60 s) and 72° C. (30 s) and this generated a product of 212 bp containing a NcoI site at its left end and a EcoRV site at its right end. The fragment is gel purified using standard procedures, cleaved with NcoI and EcoRV and ligated into the NcoI and EcoRV sites of pUC21 to obtain pUCOTSB.

Plasmid pUCOTSB is then digested with SpeI and EcoRV, the 210 bp fragment containing the 5' end of the OtsB gene is gel purified and ligated with pCGN4467 that had previously been digested with XbaI and EcoRV to obtain pCGNOTSB containing the entire OtsB gene. Plasmid pCGNOTSB is digested with NcoI and SacI, the 0.8 kb long fragment containing the OtsB gene is gel purified and ligated into the NcoI and SacI sites of pJG203 between a 903 bp long tobacco PR-1a promoter and the nos gene termination signals, yielding pPR1OTSB containing the OtsB gene fused to the tobacco PR-1a promoter.

Example 3

Preparation of a Binary Vector Containing the OtsA Gene Fused to the Tobacco PR-1a Promoter and the OtsB Gene Fused to the Tobacco PR-1a Promoter Plasmid pPR1OTSA is digested with XhoI, the protruding ends are filled-in with Klenow DNA polymerase (Promega, Madison, Wis.) and then further digested with SpeI. The resulting 2.6 kb long fragment is gel purified and ligated into the filled-in EcoRI site and the SpeI site of pPR1OTSB to obtain pPR1OTSAB, containing the OtsA gene fused to the tobacco PR-1a promoter and the OtsB gene fused to the tobacco PR-1a promoter.

Plasmid pPR1OTSAB is digested with ApaI and XbaI, the 4.6 kb long fragment containing the OtsA gene fused to the tobacco PR-1a promoter and the OtsB gene fused to the tobacco PR-1a promoter is gel purified and ligated into the ApaI and XbaI sites of pBHYGM to obtain binary vector pEGL502 (PBHYGM is a modified pGPTV-Hyg (Becker et al. (1992) Plant Mol. Biol. 20, 1195–1197) vector produced by insertion of a polylinker containing BfrI/ApaI//ClAI/

SmaI/BfrI/XbaI/SalI/PstI/SphI/HindIII restriction sites in the EcoRI and XbaI sites of pGPTV-Hyg).

Example 4

Preparation of a Binary Vector Containing the OtsA Gene Fused to the Tobacco PR-1a Promoter Plasmid pPR1OTSA is digested with ApaI and XbaI, the 2.6 kb long fragment containing the OtsA gene fused to the tobacco PR-1a promoter is gel purified and ligated into the ApaI and XbaI sites of pBHYGM to obtain a binary vector containing the OtsA gene fused to the tobacco PR-1a promoter.

Example 5

Preparation of a Binary Vector Containing the OtsB Gene Fused to the Tobacco PR-1a Promoter Plasmid pPR1OTSB is digested with ApaI and XbaI, the 2.0 kb long fragment containing the OtsB gene fused to the tobacco PR-1a promoter is gel purified and ligated into the ApaI and XbaI sites of pBHYGM to obtain a binary vector containing the OtsB gene fused to the tobacco PR-1a promoter.

Example 6

Transformation of Tobacco Leaf Discs by *A. tumefaciens*

The binary vector constructs are transformed into *A. tumefaciens* strain GV3101 (Bechtold, N. et al. (1993), CR Acad. Sci. Paris, Sciences de la vie, 316:1194–1199) by electroporation (Dower, W. J. (1987), Mol. Biol. Rep 1:5). Leaf discs of *Nicotiana tabacum* cv 'Xanthi nc' and of transgenic line "NahG" overexpressing a salicylate hydroxylase gene (Gaffney et al. (1993) Science 261: 754–756) are cocultivated with Agrobacterium clones containing the above mentioned constructs (Horsch et al. (1985), Science 227: 1229–1231) and transformants are selected for resistance to 50 mg/ml hygromycin B. Approximatively 50 independent hygromycin lines ($T_0$ lines) for each construct are selected and rooted on hormone-free medium.

Example 7

Selection of Transgenic Lines with Inducible trehalose Biosynthetic Gene Expression For each transgenic line a leaf punch of approximatively 2–3 cm² is incubated for 2 days in 3 ml of benzo(1,2,3) thiadiazole-7-carbothioic acid S-methyl ester (BTH, 5.6 mg/10 ml) under ca. 300 mmol/m$^{-2}$ s$^{-1}$ irradiants. Leaf material is harvested, flash frozen and ground in liquid nitrogen. Total RNA is extracted (Verwoerd et al. (1989) NAR 17, 2362) and Northern blot analysis is carried out as described (Ward et al. (1991) The Plant Cell 3, 1085–1094) using radiolabelled probes specific for the OtsA and OtsB genes. Transgenic lines with high inducible expression of the trehalose biosynthetic genes in presence of the chemical inducer and low background expression in absence of the chemical inducer are selected. In particular, two transgenic lines are selected N5 and N6 and self-pollinated, and their progeny is used for further analysis.

Example 8

Transformation of Maize

The method used for maize transformation has been described by Koziel et al. (Biotechnology 11, 194–200, 1993) using particle bombardment into cells of immature embryos. Transformation of maize with at least one of the plasmids described herein is achieved by microprojectile bombardment of either immature zygotic embryos or serially-propagatable Type I embryogenic callus.

Type I embryogenic callus cultures (Green et al., Miami Winter Symposium 20,1983) of the proprietary genotype CG00526 and CG00714 are initiated from immature embryos, 1.5–2.5 mm in length, from greenhouse grown material. Embryos are aseptically excised from surface-sterilized ears approximately 14 days after pollination. Embryos of CG00526 are placed on D callus initiation media with 2% sucrose and 5 mg/L chloramben (Duncan et al., Planta 165: 322–332, 1985) while those of CG00714 are placed onto KM callus initiation media with 3% sucrose and 0.75 mg/L 2,4-d (Kao and Michayluk, Planta 126:105–110, 1975). Embryos and embryogenic cultures are subsequently cultured in the dark. Embryogenic responses are removed from the explants after ~14 days. CG00526 responses are placed onto D callus maintenance media with 2% sucrose and 0.5 mg/L 2,4-d while those of CG00714 are placed onto KM callus maintenance media with 2% sucrose and 5 mg/L Dicamba. After 3 to 8 weeks of weekly selective subculture to fresh maintenance media, high quality compact embryogenic cultures are established. Actively growing embryogenic callus pieces are selected as target tissue for gene delivery. The callus pieces are plated onto target plates containing maintenance medium with 12% sucrose approximately 4 hours prior to gene delivery. The callus pieces are arranged in circles, with radii of 8 and 10 mm from the center of the target plate.

Plasmid DNA is precipitated onto gold microcarriers as described in the DuPont Biolistics manual. Two to three μg of each plasmid is used in each 6 shot microcarrier preparation. Genes are delivered to the target tissue cells using the PDS-100He Biolistics device. The settings on the Biolistics device are as follows: 8 mm between the rupture disc and the macrocarrier, 10 mm between the macrocarrier and the stopping screen and 7 cm between the stopping screen and the target. Each target plate is shot twice using 650 psi rupture discs. A 200×200 stainless steel mesh (McMaster-Carr, New Brunswick, N.J.) is placed between the stopping screen and the target tissue.

Seven days after gene delivery, target tissue pieces are transferred from the high osmotic medium to high level selection media. All amino acids are removed from the selection media. After 5 to 8 weeks on these high level selection media, any growing callus from CG00526 is subcultured to low to medium level media.

Tissue surviving selection from an original target tissue piece is subcultured as a single colony and designated as an independent transformation event.

At that point, colonies selected on selection media are transferred to a modified MS medium (Murashige and Skoog, Physiol. Plant, 15:473–497, 1962) containing 3% sucrose (MS3S) with no selection agent and placed in the light. For CG00526, 0.25 mg/L ancymidol and 0.5 mg/L kinetin are added to this medium to induce embryo germination while for CGO0714, 2 mg/L benzyl adenine is added.

Regenerating colonies are transferred to MS3S media without ancymidol and kinetin or benzyl adenine after 2 weeks. Regenerating shoots with or without roots from all colonies are transferred to Magenta boxes containing MS3S medium and small plants with roots are eventually recovered and transferred to soil in the greenhouse.

Transformation events have also been created using Type I callus obtained from immature zygotic embryos using standard culture techniques. For gene delivery, approximately 300 mg of the Type I callus is prepared by subculturing to fresh media 1 to 2 days prior to gene delivery, selecting target tissue pieces and placing them in a ring pattern 10 mm from the center of the target plate on medium again containing 12% sucrose. After approximately 4 hours, the tissue is bombarded using the PDS-1000/He Biolistic device from DuPont. The plasmids are precipitated onto 1 um gold particles using the standard protocol from DuPont. Genes are delivered using two shots per target plate at 650 psi. Approximately 16 hours after gene delivery the callus is transferred to standard culture medium containing 2% sucrose with no selection agent. At 12 or 13 days after gene delivery, target tissue pieces are transferred to selection media containing 40 mg/l phosphinothricin as either Basta or bialaphos. The callus is subcultured on selection for 12 to 16 weeks, after which surviving and growing callus is transferred to standard regeneration medium.

Example 9

Transformation of Wheat

Transformation of immature embryos and immature embryo-derived callus using particle bombardment has been described by Vasil et. al. (Biotechnology 11: 1553–1558, 1993) and Weeks et. al. (Plant Physiology 102: 1077–1084, 1993).

A preferred technique for wheat transformation involves particle bombardment of immature wheat embryos and includes either a high sucrose or a high maltose step prior to gene delivery. Prior to bombardment, any number of embryos (0.75–1 mm in length) are plated onto MS medium with 3% sucrose (Murashige and Skoog, 1962) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid is precipitated onto micrometer size gold particles using standard procedures. Each plate of embryos is shot with the DuPont Biolistics helium device using a burst pressure of ~1000 psi and using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent. After about one month, developed shoots are transferred to larger sterile containers known as GA7s which contained half-strength MS, 2% sucrose, and the same concentration of selection agent. The stable transformation of wheat is described in detail in patent application EP 0 674 715.

Example 10

Transformation of Rice

Immature spikelets with milky endosperm of the Japonica rice variety "Taipei 309" are dehulled and surface sterilized with 70% (v/v) ethanol for 1 min and 6% calcium hypochlorite for 20 min, followed by three ishes with sterile distilled water.

The isolated immature embryos are cultured at 28° C. on 0.35% agarose-solidified MS-medium (Murashige and Skoog, 1962) containing 3% sucrose, 2 mg/l 2,4-dichlorophenoxyacetic acid (2,4-D), pH 5.8. After one week, callus material produced from the scutella is divided and cultured by weekly transfers onto fresh medium. Four weeks after the initiation, three to four calli are transferred into a 50-ml-culture vessel containing 20 ml of R2-medium (R2 salts and vitamins [Ohira et al. 1973], 1 mg/l 2,4-D, 500 mg/l 2-morpholino ethanesulfonic acid [MES], 3% sucrose, pH 5.8). The cultures are maintained in dim light at 28° C. on a rotary shaker at 220 rpm, and the medium is replaced weekly by an equal amount of fresh medium. Rapidly dividing, friable calli are selected and subcultured into a fresh container by transferring 2 ml of fine callus suspension into 20 ml of R2-medium.

Two- to 3-month-old suspension cultures that have been subcultured 3 to 4 days in advance serve as target cells for the bombardments. Four hours before particle bombardment, approx. 500 mg of cells are spread as a single layer of 2 cm in diameter on 0.35% agarose-solidified piasmolysis medium (R2 salts and vitamins, 1 mg/l 2,4-D, 3% sucrose, 0.5 M sucrose, pH 5.8) contained in a 5.5-cm petri dish.

A particle inflow gun (Finer et al., 1992) is used to deliver DNA-coated gold particles (Aldrich Cat. # 32,658-5, spherical gold powder 1.5–3.0 µm) into the embryogenic suspension cells. Particle coating is essentially performed as described by Vain et al. (1993): 5 µl aliquots of the plasmid solution are distributed into 0.5 ml-reaction tubes and placed on ice. Particles are suspended in 96% ethanol at 100 mg/ml and vortexed for 2 min. Ethanol is replaced by an equal volume of sterile ddH$_2$O and the suspension vortexed for 1 min. This washing step has to be repeated once. The particles are finally resuspended in sterile ddH$_2$O at 100 mg/ml. 25 µl of the particle suspension are added to each of the DNA aliquots and the tubes vortexed for 1 min, followed by immediate addition of 25 µl of sterile, ice-cold CaCl$_2$ (2.5 M in ddH$_2$O) and further vortexing for 1 min. 10 µl of sterile spermidine (0.1 M in ddH$_2$O) are added, the suspension vortexed again and placed on ice for 5 min during which the particles sediment. 50 µl of the particle-free supernatant are removed and the remaining suspension (15 µl) used for 5 bombardments. Prior to each bombardment, the particles need to be resuspended by intense pipetting.

The cells are covered with a 500 µm mesh baffle and positioned at 14 cm below the filter unit containing the particles. Particles are released by a single 8-bar-pressure pulse of 50 msec in partial vacuum ($2 \times 10^4$ Pa).

24 h post bombardment with one of the transformation vectors mentioned, the cells are transferred onto 0.3% agarose-solidified, selective callus increasing medium R2l (R2 salts, 1 mg/l 2,4-D, 1 mg/l thiamine-HCl, 500 mg/l MES, 6% sucrose, pH 5.8) containing a suitable selection agent such as, for example, 30 mg/l paromomycin, and maintained at 280° C. in darkness for 3 weeks until the paromomycin-resistant (Pam$^R$) colonies become visible under the stereo microscope. Pam$^R$ colonies are transferred onto fresh R21 medium containing 40 mg/l paromomycin and cultured in darkness (weekly subculture). After 2 weeks, Pam$^R$ colonies are transferred to 0.5% agarose-solidified R21 containing 40 mg/l paromomycin and cultured for 1 week in darkness. For regeneration, colonies are then transferred onto 0.8% agarose-solidified shoot induction medium (R2R: R2 salts, MS vitamins, 2% sucrose, 3% sorbitol, 1 mg/l zeatin, 0.5 mg/l IAA, 40 mg/l paromomycin) and cultured in light until shoots are formed. In parallel, callus material is maintained on R21 medium containing 40 mg/l paromomycin and cultured in darkness with weekly subcultures in order to obtain homoplasmic cell lines.

B. Expression of the Trehalose-6-phosphate Synthase and Trehalose-6-phosphate Phosphatase Genes in the Plant Plastid B1. Inducible Expression Example 11

Construction of Vector pAT236 for Homologous Recombination into the Plastid Genome The tmV and rps12/7 intergenic region of the tobacco plastid genome is modified for insertion of chimeric genes by homologous recombination. A 1.78 kb region (positions 139255 to 141036, Shinozaki et al. (1986) *EMBO J.* 5:2043–2049) is PCR amplified from the tobacco plastid genome and a PstI site is inserted after position 140169, yielding 915 bp and 867 bp of flanking plastid DNA 5' and 3' of the PstI insertion site. PCR amplification (Pfu Turbo DNA Polymerase, Stratagene, La Jolla, Calif.) is performed with a primer pair inserting a BsiEI site before position 139255 (5'-TAA CGG CCG CGC CCA ATC ATT CCG GAT A-3', SEQ ID No:5) and a PstI site after position 140169 (5'-TAA CTG CAG AAA GAA GGC CCG GCT CCA A-3', SEQ ID No:6). PCR amplification is also performed with a primer pair inserting a PstI site before position 140170 (5'-CGC CTG CAG TCG CAC TAT TAC GGA TAT G-3', SEQ ID No:7) and a BsiWI site after position 141036 (5'-CGC CGT ACG AAA TCC TTC CCG ATA CCT C-3', SEQ ID No:8). The PstI—BsiEI fragment is inserted into the PstI-SacII sites of pbluescript SK+ (Stratagene), yielding pAT216 and the PstI-BsiWI fragment is inserted into the PstI-Acc651 sites of pbluescript SK+, yielding pAT215. PAT218 contains the 1.78 kb of plastid DNA with a PstI site for insertion of chimeric genes and selectable markers and is constructed by ligation of the 2.0 kb PstI-ScaI fragment of pAT215 and the 2.7 kb PstI-ScaI band of pAT216.

I. Amplification of the Tobacco 16S rRNA Promoter and rbs of the rbcL Gene

The 16S rRNA promoter is PCR amplified from tobacco DNA (*N. tabacum* cv. Xanthi) and fused to a synthetic ribosome binding site (rbs) of the tobacco plastid rbcL gene. The "top strand" primer inserts an EcoRI site at the 5' end of the 16S rRNA promoter before position 102568 (5'-GCC AGA ATT CGC CGT CGT TCA ATG AGA ATG-3', SEQ ID NO:9). The "bottom strand" primer amplifies up to position 102675 of the 16S rRNA promoter, removes two upstream ATG's by changing positions 102661 (A to C) and 102670 (A to C), adds the rbs of the rbcL gene (positions 57569–57584) as a 5' extension of the primer and inserts a BspHI site at the 3' end of the rbs (5'-GCC TTC ATG ATC CCT CCC TAC AAC TAT CCA GGC GCT TCA GAT TCG-3', SEQ ID NO:10). The 142 bp amplification product is gel purified and cleavage with EcoRI and BspHI yields a 128bp fragment containing the tobacco 16S rRNA promoter fused to the rbs of the rbcL gene.

II. Amplification of the Tobacco Plastid rps16 Gene 3' Untranslated RNA Sequence (3'UTR)

The tobacco plastid rps16 3' UTR is PCR amplified from tobacco DNA (*N. tabacum* cv. Xanthi) using the following oligonucleotide pair: a SpeI site is added immediately after the stop codon of the plastid rps16 gene encoding ribosomal protein S16 with the "top strand" primer (5' CGC GAC TAG TTC AAC CGA AAT TCA AT-3', SEQ ID NO:11) and a PstI site is added at the 3' end of the rps16 3' UTR with the "bottom strand" primer (5'-CGC TCT GCA GTT CAA TGG AAG CAA TG-3', SEQ ID NO:12). The amplification product is gel purified and digested with SpeI and PstI, yielding a 163 bp fragment containing the tobacco rps6 3' UTR (positions 4941 to 5093 of the tobacco plastid genome, Shinozaki et al., 1986) flanked 5' by a SpeI site and 3' with a PstI site.

III. Construction of a 16S rRNA Promoter::aadA Gene::rps16 3'UTR Cassette for Plastid Transformation Selection The coding sequence of the aadA gene, a bacterial gene encoding the enzyme aminoglycoside 3" adenyltransferase that confers resistance to spectinomycin and streptomycin, is isolated from pRL277 (Black et al. (1993) Molecular Microbiology 9:77–84 and Prentki et al. (1991) Gene 103: 17–23). The 5' major portion of the aadA coding sequence is isolated as a 724 bp BspHI-BssHII fragment from pRL277 (the starting codon is at the BspHI site) and the 3' remainder of the aadA gene is modified by adding a SpeI site 20 bp after the stop codon by PCR amplification using pRL277 as template and the following oligonucleotide pair: the "top strand" primer (5'-ACC GTA AGG CTT GAT GAA-3', SEQ ID NO:13) and the "bottom strand" primer which add a SpeI site (5'-CCC ACT AGT TTG AAC GAA TTG TTA GAC-3', SEQ ID NO:14). The 658 bp amplification product is gel purified, digested with BssHII, SpeI and the 89 bp fragment is ligated to the 5' portion of the aadA gene carried on a 724 bp BspHI-BssHII fragment, the 16S rRNA promoter and rbs of rbcL carried on a 128 bp EcoRI-BspHI PCR amplified fragment and EcoRI-SpeI digested pLITMUS28 vector (New England Biolabs), yielding pAT223. A three-way ligation is performed on an EcoRI-SpeI 0.94 kb fragment of pAT223 containing the 16S rRNA promoter-rbs driven aadA gene, a 163 bp SpeI, PstI digested PCR fragment containing the rps16 3' UTR and puc19 (New England Biolabs) cut with EcoRI, PstI to obtain pAT229 containing the 16S rRNA promoter driving the aadA gene with the rps16 3'UTR.

IV. Amplification of the Bacteriophage T7 Gene 10 Promoter

The bacteriophage T7 gene 10 promoter is PCR amplified from pET-3d (Statagene) using the following oligonucleotide pair: the "top strand" primer inserted an EcoRI site at the 5' end of the T7 promoter (5'-CCC GAA TTC ATC CCG CGA AAT TAA TA-3', SEQ ID NO:15) and the "bottom strand" primer inserted a NcoI site at the 3' end (5'-CGG CCA TGG GTA TAT CTC CTT CTT AAA GTT AAA-3', SEQ ID NO:16). The amplification product is gel purified and cleavage with EcoRI, NcoI produces a 96 bp fragment containing the T7 promoter.

V. Amplification of the Bacteriophage T7 Gene 10 Terminator

The bacteriophage T7 gene 10 terminator is PCR amplified from pET-3d (Stratagene) using the following oligonucleotide pair: the "top strand" primer inserts a HindIII site at the 5' end of the terminator (5'-GCG AAG CTT GCT GAG CAA TAA CTA GCA TAA-3', SEQ ID NO:17) and the "bottom strand" primer inserts a PstI site at the 3' end of the terminator (5'-GCG CTG CAG TCC GGA TAT AGT TCC TCC T-3', SEQ ID NO:18). The amplification product is gel purified and cleavage with HindIII-PstI produces a 86 bp fragment containing the T7 terminator.

VI. Amplification of the *Arabidopsis Thaliana* Plastid psbA 3' Untranslated RNA Sequence The *A. thaliana* plastid psbA 3' UTR is PCR amplified from *A. thaliana* DNA (ecotype Landsburg) using the following oligonucleotide pair: the "top strand" primer adds a SpeI site to the 5' end of the 3' UTR and eliminates a XbaI site in the native sequence by mutating a G to an A (underlined) (5'-GCG ACT AGT TAG TGT TAG TCT AAA TCT AGT T-3', SEQ ID NO:19) and the "bottom strand" primer adds a HindIII site to the 3' end of the UTR (5'-CCG CAA GCT TCT AAT AAA AAA TAT ATA GTA-3', SEQ ID NO:20). The amplified region extends from position 1350 to 1552 of GenBank accession number X79898. The 218 bp PCR product is gel purified, digested with SpeI and HindIII and ligated with the HindIII-PstI cut PCR fragment carrying the T7 terminator into the SpeI-PstI sites of pbluescript sk- (Stratagene), yielding pPH171. Sequence analysis of the psbA 3' UTR region of pPH171 compared to GenBank accession number X79898 reveals deletion of an A at positions 1440 and 1452.

VII. Preparation of a Chimeric Gene Containing the GUS Reporter Gene Fused to a Bacteriophage T7 Gene 10 Promoter and Terminator and the Arabidopsis Plastid psbA 3'UTR in a Plastid Transformation Vector A bacteriophage T7 gene 10 promoter:: GUS gene:: *A. thaliana* psbA 3' UTR :: T7 terminator cassette is constructed with a four-way ligation of the 96 bp EcoRI, NcoI PCR fragment containing the T7 promoter, a 1.86 kb NcoI, XbaI fragment from pC8 containing the GUS gene, and the 295 bp XbaI, PstI fragment of pPH171 containing the *A. thaliana* psbA 3' UTR and T7 terminator into the EcoRI, PstI sites of pGEM-3Z (Stratagene), yielding plasmid pAT221. The T7 promoter driven GUS gene cassette is ligated to the aadA selectable marker cassette by cloning the 1.1 kb HindIII, EcoRI fragment of pAT229 containing the 16S rRNA promoter-rbs :: aadA :: rps16 3' UTR cassette and the 2.26 kb EcoRI, PstI pAT221 fragment carrying the T7 promoter :: GUS :: psbA 3' UTR :: T7 terminator cassette into the HindIII, PstI sites of pbluescript sk+ (Stratagene), producing plasmid pAT232. Plastid transformation vector pAT236 is constructed by ligating the 3.36 kb PstI band from pAT232 containing the GUS and selectable marker cassettes into the PstI site of pAT218 and screening for an insert orientation where the GUS gene is transcribed in the same direction as the rps12/7 ORF.

Example 12

Construction of a Vector Using a Polyguanosine Tract as a Substitute for a 3'UTR A polyguanosine tract has been shown to substitute for the plastid atpB gene 3' UTR in vivo (Drager et al. (1996) RNA 2:652–663). A poly G tract containing 18 consecutive guanosine residues flanked by SpeI, HindIII sticky ends on the 5' and 3' ends respectively is assembled by annealing the following two kinased oligonucleotides: (5'-CTA GTG GGG GGG GGG GGG GGG GGA-3', SEQ ID NO:21) and (5'-AGC TTC CCC CCC CCC CCC CCC CCA-3', SEQ ID NO:22). The polyG$_{18}$ tract containing SpeI, HindIII sticky ends is ligated with the HindIII, PstI digested PCR fragment containing the T7 terminator into the SpeI, PstI sites of pBluescript SK+ (Stratagene).

Example 13

Preparation of a Chimeric Gene Containing the *E. coli* Trehalose-6-phosphate Synthase Gene (OtsA) Fused to the Phage T7 Gene 10 Promoter in a Plastid Transformation Vector Genomic DNA from *E. coli* strain DH5-alpha is used as template for PCR amplification of the 5' portion of the OtsA gene with a top strand primer incorporating the ATG start codon followed by a newly added GCA codon, thus creating an NcoI restriction site (primer pOTSAN+: 5'-TGA CCA TGG CAA GTC GTT TAG TCG TAG T-3', SEQ ID NO:23), and a bottom strand primer downstream of the unique SfuI restriction site in OtsA (pOTSAN-: 5'-AGC AAC GCT TCA TAG-3', SEQ ID NO:24). PCR reactions are undertaken in 50 ul volumes using PFU DNA polymerase (Promega) as recommended by the manufacturer in a DNA Thermocycler 480 (Perkin Elmer/Roche, Branchburg, N.J.) for five cycles at 94° C. (30 s), 40° C. (60 s), and 72° C. (30 s) followed by 25 cycles at 94° C. (30 s), 55° C. (60 s) and 72° C. (30 s). The 850 bp PCR product is gel purified using standard procedures and cleaved with NcoI (all restriction enzymes obtained from New England Biolabs except where otherwise noted) and SfuI (Boehringer Mannheim, Corp., Indianapolis) to release a 661 bp DNA fragment. The 3' portion of OtsA is obtained in a similar manner as described above using a top strand primer (pOTSAX+: 5'-GCG TTC CTG GAT TGT C-3', SEQ ID NO:25) located upstream of the SfuI site in OtsA, and a bottom strand primer (pOTSAX-: 5'-GGG TCT AGA GAT TCA CGC GAG CTT TGG AAA GGT AGC A-3', SEQ ID NO:26) that introduces an XbaI restriction site downstream of the stop codon and destroys the HindIII restriction site present at the 3' end of OtsA by changing the CTT Leu codon to CTC. The 861 bp amplification product is gel purified, digested with SfuI and XbaI, and the resulting 772 bp DNA fragment ligated with the 5' OtsA NcoI/SfuI fragment in pLitmus28 (Promega) digested with NcoI and XbaI to create pOTSA.

Plasmid DNA from pAT236 (Example 11), containing a phage T7 gene 10 promoter cassette from pET3a (Novagen) in a plastid transformation vector, is digested with NcoI and SphI (to create a 1646 bp fragment) and SphI and XbaI (to create a 4514 bp fragment). These vector fragments are ligated in a three-way reaction with the 1433 bp NcoII/XbaI fragment of pOTSA that contains the complete OtsA gene to create plastid transformation vector pT7-OTSA.

Example 14

Preparation of a Chimeric Gene Containing the *E. coli* Trehalose-6-phosphate Phosphatase Gene (OtsB) Fused to the Phage T7 Gene 10 Promoter in a Plastid Transformation Vector The 5' portion of the OtsB gene is amplified from *E. coli* genomic DNA as described above using top strand primer pOTSBN+: 5'-GTC GCC ATG GTG ACA GAA CCG TTA ACC-3', SEQ ID NO:27, that converts the GTG start codon of OtsB to ATG and adds a GTG Val codon at the second position, and bottom strand primer pOTSBN-: 5'-GTT CGC CCG ATA AAG GGA G-3', SEQ ID NO:28, located downstream of the unique BglII site of OtsB. The 584 bp product is gel-purified and digested with NcoI and BglII and the resulting 459 bp fragment isolated. The 3' portion of OtsB is similarly amplified using top strand primer pOTSBX+: 5'-TAG CGC AAC GTA TTA CTC-3', SEQ ID NO:29, located upstream of the OtsB BglII site, and bottom strand primer pOTSBX−: 5'-GCC TCT AGA CTC ATC ATT AGA TAC TAC GAC TAA AC-3', SEQ ID NO:30, that incorporates an XbaI restriction site downstream of the OtsB stop codon. The gel-purified 381 bp product is digested with BglII and XbaI, and the resulting 354 bp BglII/XbaI restriction fragment ligated with the 5' OtsB NcoI/BglII restriction fragment into vector pLitmus28 digested with NcoI and XbaI to create pOTSB.

Plasmid pOTSB is then digested with NcoI and XbaI and the resulting 820 bp fragment containing the complete OtsB gene is ligated in a three-way reaction with the NcoI/SphI and SphI/XbaI fragments of plasmid pAT236 as described above to create plastid transformation vector pT7_OTSB.

Example 15

Preparation of a Plastid Transformation Vector Containing an Operon-like Chimeric Gene Construct Containing the OtsA and the OtsB Genes Fused to a Bacteriophage T7 Promoter and Terminator Plasmid pOTSB is digested with NcoI and SpeI and the 3534 bp vector backbone/OtsB fragment isolated and dephosphorylated. This fragment is ligated to a synthetic oligonucleotide linker containing a portion of the phage T7 gene 10 5' UTR and a chimeric consensus plastid ribosome binding site prepared by annealing and then phosphorylating with T4 kinase the top strand oligonucleotide 5'-CTAGTG GGA GAC CAC AAC GGT TTC CCT CTA GAA ATA ATT TTG TTT AAG TTT AAG AAG GGG AGA GAA T-3', SEQ ID NO:31 (SpeI restriction site overhang underlined) and the bottom strand oligonucleotide 5'-CATGAT TCT CTC CCC TTC TTA AAC TTA AAC AAA ATT ATT TCT AGA GGG AAA CCG TTG TGG TCT CCC A-3', SEQ ID NO:32 (BspHI restriction site overhang underlined). The resulting plasmid pOTSBL is digested with SpeI and ligated to a 1516 bp SpeI/XbaI fragment of pOTSA selected for the orientation SpeI—OtsA::linker::OtsB to create pOTSABL. Plasmid pOTSABL is then digested with NcoI and XbaI (partial) and the resulting 2313 bp fragment containing the complete OtsA::T75'/RBS::OtsB cassette is ligated in a three-way reaction with the NcoI/SphI and SphI/XbaI fragments of plasmid pAT236 as described above to create plastid transformation vector pT7_OTSAB.

A similar plastid transformation vector comprising omitting the portion of the phage T7 gene 10 5' UTR is also created using standard methods in molecular biology.

B2. Constitutive Expression

Example 16

Amplification of the Tobacco Plastid clpP Gene Promoter and Complete 5' Untranslated RNA (5'UTR).

Total DNA from *N. tabacum* c.v. "Xanthi NC" is used as the template for PCR with a left-to-right "top strand" primer comprising an introduced EcoRI restriction site at position −197 relative to the ATG start codon of the constitutively expressed plastid clpP gene (primer Pclp_P1a: 5'-GCG GAATTC ATA CTT ATT TAT CAT TAG AAA G-3' (SEQ ID NO:33); EcoRI restriction site underlined) and a right-to-left "bottom strand" primer homologous to the region from −21 to −1 relative to the ATG start codon of the clpP promoter that incorporates an introduced NcoI restriction site at the start of translation (primer Pclp_P2b: 5'-GCG CCATGG TAA ATG AAA GAA AGA ACT AAA-3' (SEQ ID NO:34); NcoI restriction site underlined). This PCR reaction is undertaken with Pfu thermostable DNA polymerase (Stratagene, La Jolla Calif.) in a Perkin Elmer Thermal Cycler 480 according to the manufacturer's recommendations (Perkin Elmer/Roche, Branchburg, N.J.) as follows: 7 min 95° C., followed by 4 cycles of 1 min 95° C./2 min 43° C./1 min 72° C., then 25 cycles of 1 min 95° C./2 min 55° C./1 min 72° C. The 213 bp amplification product comprising the promoter and 5' untranslated region of the clpP gene containing an EcoRI site at its left end and an NcoI site at its right end and corresponding to nucleotides 74700 to 74505 of the *N. tabacum* plastid DNA sequence (Shinozaki et al., *EMBO J.* 5: 2043–2049 (1986)) is gel purified using standard procedures and digested with EcoRI and NcoI (all restriction enzymes are purchased from New England Biolabs, Beverly, Mass.).

Example 17

Amplification of the Tobacco Plastid rps16 Gene 3' Untranslated RNA Sequence

Total DNA from *N. tabacum* c.v. "Xanthi NC" is used as the template for PCR as described above with a left-to-right "top strand" primer comprising an introduced XbaI restriction site immediately following the TAA stop codon of the plastid rps16 gene encoding ribosomal protein S16 (primer rps16P_1a (5'-GCG TCTAGA TCA ACC GAA ATT CAA TTA AGG-3' (SEQ ID NO:35); XbaI restriction site underlined) and a right-to-left "bottom strand" primer homologous to the region from +134 to +151 relative to the TAA stop codon of rps16 that incorporates an introduced HindIII restriction site at the 3' end of the rps16 3' UTR (primer rps16P_1b (5'-CGC AAGCTT CAA TGG AAG CAA TGA TAA-3' (SEQ ID NO:36); HindIII restriction site underlined). The 169 bp amplification product comprising the 3' untranslated region of the rps16 gene containing an XbaI site at its left end and a HindIII site at its right end and containing the region corresponding to nucleotides 4943 to 5093 of the *N. tabacum* plastid DNA sequence (Shinozaki et al., 1986) is gel purified and digested with XbaI and HindIII.

Example 18

Preparation of a Plastid Transformation Vector Containing a GUS Reporter Gene Fragment Ligated to the clpP Gene Promoter and 5' and 3' UTR's.

An 1864 bp b-galacturonidase (GUS) reporter gene fragment derived from plasmid pRAJ275 (Clontech) containing an NcoI restriction site at the ATG start codon and an XbaI site following the native 3' UTR is produced by digestion with NcoI and XbaI. This fragment is ligated in a four-way reaction to the 201 bp EcoRI/NcoI cipP promoter fragment, the 157 bp XbaI/HindIII rps16 3'UTR fragment, and a 3148 bp EcoRI/HindIII fragment from cloning vector pGEM3Zf (−) (Promega, Madison Wis.) to construct plasmid pPH138. Plastid transformation vector pPH140 is constructed by digesting plasmid pPRV111a (Zoubenko et al. (1994)

Nucleic Acids Res 22:3819–24) with EcoRI and HindIII and ligating the resulting 7287 bp fragment to a 2222 bp EcoRI/HindIII fragment of pPH138.

Example 19

Preparation of a Plastid Transformation Vector Containing the OtsA Gene Ligated to the clpP Gene Promoter and 5' and 3' UTR's.

A 1433 bp NcoI/XbaI fragment of pOTSA that contains the complete OtsA gene is ligated in a four-way reaction to the 201 bp EcoRI/NcoI clpP promoter fragment, the 157 bp XbaI/HindIII rps16 3'UTR fragment, and a 3148 bp EcoRI/HindIII fragment from cloning vector pGEM3Zf(−) (Promega, Madison Wis.) to construct plasmid pclpOtsA. A plastid transformation vector is constructed by digesting plasmid pPRV111a with EcoRI and HindIII and ligating the resulting 7287 bp fragment to a 1791 bp EcoRI/HindIII fragment of pclpOtsA.

Example 20

Preparation of a Plastid Transformation Vector Containing the OtsB Gene Ligated to the clpP Gene Promoter and 5' and 3' UTR's.

Plasmid pOTSB is digested with NcoI and XbaI and the resulting 820 bp fragment containing the complete OtsB gene is ligated in a four-way reaction to the 201 bp EcoRI/NcoI clpP promoter fragment, the 157 bp XbaI/HindIII rps16 3' UTR fragment, and a 3148 bp EcoRI/HindIII fragment from cloning vector pGEM3Zf(−) (Promega, Madison Wis.) to construct plasmid pclpOtsB. A plastid transformation vector is constructed by digesting plasmid pPRV111a with EcoRI and HindIII and ligating the resulting 7287 bp fragment to a 1178 bp EcoRI/HindIII fragment of pclpOtsB.

Example 21

Preparation of a Plastid Transformation Vector Containing an Operon-like Chimeric Gene Construct Containing the OtsA Gene and OtsB Gene Ligated to the clpP Gene Promoter and 5' and 3' UTR's.

Plasmid pOTSABL is digested with NcoI and XbaI (partial) and the resulting 2313 bp fragment containing the complete OtsA::T75'/RBS::OtsBcassette is ligated in a four-way reaction to the 201 bp EcoRI/NcoI clpP promoter fragment, the 157 bp XbaI/HindIII rps16 3'UTR fragment, and a 3148 bp EcoRI/HindIII fragment from cloning vector pGEM3Zf(−) (Promega, Madison Wis.) to construct plasmid pclpOtsAB. Plastid transformation vector pPH140 is constructed by digesting plasmid pPRV111a (Zoubenko et al. 1994) with EcoRI and HindIII and ligating the resulting 7287 bp fragment to a 2671 bp EcoRI/HindIII fragment of pclpOtsAB.

Example 22

Biolistic Transformation of the Tobacco Plastid Genome

Seeds of Nicotiana tabacum c.v. 'Xanthi nc' are germinated seven per plate in a 1" circular array on T agar medium and bombarded 12–14 days after sowing with 1 μm tungsten particles (M10, Biorad, Hercules, Calif.) coated with DNA from plasmids pC8E5 and pC+E5 essentially as described (Svab, Z. and Maliga, P. (1993) PNAS 90, 913–917). Bombarded seedlings are incubated on T medium for two days after which leaves are excised and placed abaxial side up in bright light (350–500 μmol photons/m$^2$/s) on plates of RMOP medium (Svab, Z., Hajdukiewicz, P. and Maliga, P. (1990) PNAS 87, 8526–8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) Plant Mol Biol Reporter 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) PNAS 91, 7301–7305) and transferred to the greenhouse.

Example 23

Preparation of Transgenic Tobacco Expressing a Chemically Inducible, Plastid-targeted T7 RNA Polymerase A synthetic oligonucleotide linker comprising an NcoI restriction site and ATG start codon followed by the first seven plastid transit peptide codons from the rbcS gene (encoding the small subunit of ribulose bisphosphate carboxylase) and endogenous PstI restriction site (top strand: 5'-CAT GGC TTC CTC AGT TCT TTC CTC TGC A-3', SEQ ID NO:37; bottom strand: 5'-GAG GAA AGA ACT GAG GAA GC-3', SEQ ID NO:38), a 2.8 kb PstI/SacI DNA fragment of pCGN4205 (McBride, K. E. et al. (1994) PNAS 91, 7301–7305) containing the bacteriophage T7 RNA polymerase gene (T7 Pol) fused in frame to the 3' portion of the rbcS gene transit peptide coding sequence, a 0.9 kb NcoI/KpnI DNA fragment of pCIB296 containing the tobacco PR-1a promoter with an introduced NcoI restriction site at the start codon (Uknes et al. (1993) Plant Cell 5, 159–169) and 4.9 kb SfiI/KpnI and 6.6 kb SacI/SfiI fragments of binary Agrobacterium transformation vector pSGCGC1 (a derivative of pGPTV-Hyg containing the polylinker from pGEM4 (Promega, Madison Wis.) cloned into the SacI/HindIII sites) are ligated to construct pPH110.

Hygromycin resistant NT-pPH110 tobacco plants are regenerated as described from shoots obtained following cocultivation of leaf disks of N. tabacum 'Xanthi' and "NahG" with GV3101 Agrobacterium carrying the pPH110 binary vector. For each transgenic line duplicate leaf punches of approximately 2–3 cm$^2$ are incubated for 2 days in 3 ml of BTH (5.6 mg/10 ml) or sterile distilled water under ca. 300 μmol/m$^2$/s irradiance. Leaf material is harvested, flash frozen and ground in liquid nitrogen. Total RNA is extracted (Verwoerd et al. (1989) NAR 17, 2362) and Northern blot analysis is carried out as described (Ward et al. (1991) The Plant Cell 3, 1085–1094) using a radiolabelled T7 RNA polymerase gene probe. Plants of nineteen NT-110X (Xanthi genetic background) and seven NT-110N (NahG genetic background) T1 lines showing a range of T7 Pol expression are transferred to the greenhouse and self pollinated. Progeny segregating 3:1 for the linked hygromycin resistance marker are selfed and homozygous T2 lines selected.

Example 24

Plastid Transformation of Maize

Type I embryogenic callus cultures (Green et al. (1983) in A. Fazelahmad, K. Downey, J. Schultz, R. W. Voellmy, eds. Advances in Gene Technology: Molecular Genetics of Plants and Animals. Miami Winter Symposium Series, Vol. 20. Academic Press, N.Y.) of the proprietary genotypes CG00526 and CG00714 are initiated from immature embryos, 1.5–2.5 mm in length, from greenhouse grown material. Embryos are aseptically excised from surface-sterilized ears approximately 14 days after pollination. Embryos of CG00526 are placed on D callus initiation media with 2% sucrose and 5 mg/L chloramben (Duncan et al. (1985) Planta 165: 322–332) while those of CG00714 are placed onto KM callus initiation media with 3% sucrose and 0.75 mg/L 2,4-d (Kao and Michayluk (1975) Planta 126, 105–110). Embryos and embryogenic cultures are subsequently cultured in the dark. Embryogenic responses are removed from the explants after ~14 days. CG00526 responses are placed onto D callus maintenance media with 2% sucrose and 0.5 mg/L 2,4-d while those of CG00714 are placed onto KM callus maintenance media with 2% sucrose and 5 mg/L Dicamba. After 3 to 8 weeks of weekly selective subculture to fresh maintenance media, high quality compact embryogenic cultures are established. Actively growing embryogenic callus pieces are selected as target tissue for gene delivery. The callus pieces are plated onto target plates containing maintenance medium with 12% sucrose approximately 4 hours prior to gene delivery. The callus pieces are arranged in circles, with radii of 8 and 10 mm from the center of the target plate. Plasmid DNA is precipitated onto gold microcarriers as described in the DuPont Biolistics manual. Two to three µg of each plasmid is used in each 6 shot microcarrier preparation. Genes are delivered to the target tissue cells using the PDS-1000He Biolistics device. The settings on the Biolistics device are as follows: 8 mm between the rupture disc and the macrocarrier, 10 mm between the macrocarrier and the stopping screen and 7 cm between the stopping screen and the target. Each target plate is shot twice using 650 psi rupture discs. A 200×200 stainless steel mesh (McMaster-Carr, New Brunswick, N.J.) is placed between the stopping screen and the target tissue.

Five days later, the bombed callus pieces are transferred to maintenance medium with 2% sucrose and 0.5 mg/L 2,4-d, but without amino acids, and containing 750 or 1000 nM Formula XVII. The callus pieces are placed for 1 hour on the light shelf 4–5 hours after transfer or on the next day, and stored in the dark at 27° C.for 5–6 weeks. Following the 5–6 week primary selection stage, yellow to white tissue is transferred to fresh plates containing the same medium supplemented with 500 or 750 nM Formula XVII. 4–5 hours after transfer or on the next day, the tissues are placed for 1 hour on the light shelf and stored in the dark at 27° C. for 3–4 weeks. Following the 3–4 week secondary selection stage, the tissues are transferred to plates containing the same medium supplemented with 500 nM Formula XVII. Healthy growing tissue is placed for 1 hour on the light shelf and stored in the dark at 27° C. It is subcultured every two weeks until the colonies are large enough for regeneration.

At that point, colonies are transferred to a modified MS medium (Murashige and Skoog (1962) Physiol. Plant 15: 473–497) containing 3% sucrose (MS3S) with no selection agent and placed in the light. For CG00526, 0.25 mg/L ancymidol and 0.5 mg/L kinetin are added to this medium to induce embryo germination, while for CG00714, 2 mg/L benzyl adenine is added. Regenerating colonies are transferred to MS3S media without ancymidol and kinetin, or benzyl adenine, for CG00526 or CG00714, respectively, after 2 weeks. Regenerating shoots with or without roots are transferred to boxes containing MS3S medium and small plants with roots are eventually recovered and transferred to soil in the greenhouse.

C. Chemical Induction of the Trehalose Biosynthetic Genes and Measurement of Trehalose Content in Plants

Example 25

Chemical Induction of the Trehalose Biosynthetic Genes

Seeds are germinated and plants are grown for 3–6 weeks in the greenhouse. They are then sprayed with 1.2 mM BTH (or as further illustrated in Friedrich et al. (1996) Plant J. 10, 61–70) or with wettable powder. Samples of plant material are harvested at different time points and flash frozen. Northern Blot analysis is carried out to monitor induction of expression of the trehalose biosynthetic genes upon treatment with BTH.

Example 26

Extraction of Soluble Sugars and Polyols from Lyophilized Tobacco Tissue

10–20 mg lyophilized tissue is extracted 3 times with 400 ml 80% methanol at 65° C. for 10 minutes after addition of 40 mg manoheptulose (internal standard). The combined supernatant (after centrifugation at 13000 rpm for 5 minutes in an Eppendorff table top centrifuge) is dried under vacuum in a Speedvac at 25° C. The dried extract is then resuspended in 700 ml milipor water and desalted by adding 50 ml of a mixed bed ion exchange resin (Serdolit micro blue and red 2:1 [v/v]). The ion exchange resin is sedimented by centrifugation at 13000 rpm and washed with 300 ml Millipore water. The combined supernatant is again dried under vacuum in a Speedvac at 25° C. The residue containing mainly sugars and polyols is now ready for analysis by HPLC or for derivatisation for the subsequent analysis by capillary GC.

Example 27

HPLC Analysis

The dried residue is resuspended in 200 ml water and centrifuged for 15 min at 15000 rpm. An aliquot of 10 ml is separated isocratically with a 100 mM NaOH solution on a Dionex P100 ion exchange column using an HPLC system from Dionex equipped with a pulsed amperometric detector.

Example 28

Capillary GC

The dried residue is resuspended in 200 ml 50% methanol and centrifuged for 15 min at 15000 rpm. 80 ml of the supernatant are transferred into 200 ml GC injection vials. The sugars and polyols are dried under vacuum in a Speedvac. The residue is then rendered anhydrous by repeated evaporation of added methanol on a heating block at 80° C. The anhydrous residue is now sealed with septa containing screw caps. The samples are then dissolved in anhydrous pyridine containing 625 mg hydroxylamine and 50 mg phenyl-b-glucopyranoside. This mixture is incubated at 80° C. for 30 minutes. After addition of 50 ml N-methyl-N-trimethylsilyl-heptafluoro-butyramide containing 1% trim-ethylchlorosilane (v/v) the derivatisation reaction is carried out for 30 minutes at 80° C. The TMS-(trimethylsilyl)-derivatives of sugars and polyols are now ready for analysis by GC. The separation of 1 to 3 ml of this reaction mixture is performed with a Carlo Erba GC equipped with a FID detector using the conditions listed below: Capillary: SW Scientific, 30 m, ID 0.323 mm, liquid Phase DB-17. Temperature program: 70° C., 2 min, 25° C./min to 170° C., 700° C./min to 340° C., 340° C., 5 min

|  | trehalose (mg/g DW) | glucose (mg/g DW) | fructose (mg/g DW) | sucrose (mg/g DW) |
|---|---|---|---|---|
| Xanthi 0 day BTH | 0 | 18.1 | 3.7 | 17.6 |
| Xanthi 3 days BTH | 0 | 6.7 | 1.5 | 9.1 |
| Xanthi 7 days BTH | 0 | 11.9 | 2.2 | 16.4 |
| N5/3 0 day BTH | 0 | 3 | 0.6 | 8.2 |
| N5/3 3 days BTH | traces | 2.4 | 0.2 | 7 |
| N5/3 7 days BTH | 0.5 | 8.4 | 1.6 | 19.5 |
| N5/3 7 days WP | 0 | 6.9 | 1.5 | 12.9 |
| N5/4 0 day BTH | 0 | 7.3 | 1.8 | 16.7 |
| N5/4 3 days BTH | traces | 1.3 | 0.4 | 7.7 |
| N5/4 7 days BTH | 0.6 | 9.5 | 2.2 | 19.7 |
| N5/4 22 days BTH | 2.3 | 24 | 4.7 | 17.6 |
| N5/4 7 days WP | 0 | 24.9 | 4 | 10.1 |
| N6/1 0 day BTH | 0 | 9.7 | 1.9 | 18.1 |
| N6/1 3 days BTH | 0 | 1.7 | 0.5 | 10.3 |
| N6/1 7 days BTH | traces | 10.7 | 2.4 | 23.6 |
| N6/1 22 days BTH | 0.7 | 31.7 | 6.2 | 13.2 |
| N6/2 0 day BTH | 0 | 3.6 | 0.6 | 11.1 |
| N6/2 3 days BTH | 0 | 4 | 1.1 | 8.6 |
| N6/2 7 days BTH | traces | 6.1 | 1.3 | 20.1 |
| N6/7 0 day BTH | 0 | 2.1 | 0.4 | 13.6 |
| N6/7 3 days BTH | 0.1 | 1.5 | 0.4 | 9.1 |
| N6/7 7 days BTH | 1.2 | 12.7 | 2.9 | 25.8 |
| N6/7 22 days BTH | 2.6 | 37 | 6.5 | 17.1 |
| N6/8 0 day BTH | 0 | 4 | 0.8 | 10.4 |
| N6/8 3 days BTH | 0 | 2.4 | 0.4 | 7.9 |
| N6/8 7 days BTH | 0.2 | 14.9 | 3.3 | 16.1 |

Example 29

Determination of the Trehalose Content in Transgenic Plants by HPLC

The progeny of two independent transgenic lines (N5/3 and N5/4 for transgenic line N5, N6/1, N6/2, N6/7 and N6/8 for transgenic line N6) are grown and treated with BTH as described in example 25. Samples are harvested and extracted as described in example 26. The trehalose content is determined by HPLC (example 27).

Table 1 shows the trehalose contents of samples after BTH treatment or after treatment with wettable powder (WP) as a control. Measurements of the trehalose content the wild-type Xanthi are also shown. The values are expressed in mg/g dry weight (DW) of the measured sample. While no trehalose is detected in the wild-type Xanthi and in transgenic plants at day 0 or after treatment with BTH, trehalose is detected after BTH treatment.

Example 30

Determination of Trehalose Content in Transgenic Plants by HPLC/GC

The progeny of two independent transgenic lines (N5/3 and N5/4 for transgenic line N5, N6/1, N6/2, N6/7 and N6/8 for transgenic line N6) are grown and treated with BTH as described in example 25. Samples are harvested and extracted as described in example 26. The trehalose content is determined by HPLC/GC (example 28).

Table 2 shows the trehalose contents of samples after BTH treatment or after treatment with wettable powder (WP) as a control. Measurements of the trehalose content the wild-type Xanthi are also shown. The values are expressed in mg/g dry weight (DW) of the measured sample. Induction of trehalose accumulation in the transgenic plant after BTH treatment is observed.

|  | mg extracted | Trehalose | Glucose | Fructose | Sucrose | Mannitol | Inositol | Manoheptulose (Int. Std. 40 pg) |
|---|---|---|---|---|---|---|---|---|
| Xanthi 0 day BTH | 5.6 area | 0 | 130626 | 137761 | 122625 | 0 | 50850 | 98724 |
|  | mg/g DW | 0 | 8.11 | 9.24 | 13.99 | 0 | 316 |  |
| Xanthi 3 days BTH | 5.5 area | 0 | 23971 | 26108 | 50252 | 0 | 67458 | 48803 |
|  | mg/g DW | 0 | 3.06 | 3.61 | 11.61 | 0 | 9.18 |  |
| Xanthi 7 days BTH | 8.7 area | 0 | 103175 | 86735 | 252532 | 0 | 156339 | 78786 |
|  | mg/g DW | 0 | 5.16 | 4.69 | 23.24 | 0 | 8.33 |  |
| N5/3 0 day BTH | 4.6 area | 0 | 25664 | 26357 | 42743 | 2139 | 23091 | 76831 |
|  | mg/g DW | 0 | 2.49 | 2.82 | 7.63 | 0.23 | 2.39 |  |
| N5/3 3 days BTH | 8.3 area | 2522 | 32522 | 25992 | 91395 | 2556 | 85370 | 78343 |
|  | mg/g DW | 0.25 | 1.72 | 1.48 | 8.87 | 0.15 | 4.8 |  |
| N5/3 7 days BTH | 10.6 area | 7341 | 115732 | 109582 | 461342 | 10312 | 156336 | 89033 |
|  | mg/g DW | 0.49 | 4.21 | 4.3 | 30.84 | 0.42 | 6.05 |  |
| N5/3 7 days WP | 6.2 area | 1053 | 46576 | 50861 | 106758 | 4329 | 91251 | 81008 |
|  | mg/g DW | 0.13 | 3.18 | 3.75 | 13.41 | 0.33 | 6.64 |  |

-continued

| | mg extracted | | Trehalose | Glucose | Fructose | Sucrose | Mannitol | Inositol | Manoheptulose (Int. Std. 40 pg) |
|---|---|---|---|---|---|---|---|---|---|
| N5/4 0 day BTH | 6 | area | 124 | 63822 | 75278 | 136497 | 6640 | 46626 | 98401 |
| | | mg/g DW | 0.01 | 3.71 | 4.73 | 14.59 | 0.43 | 2.88 | |
| N5/4 3 days BTH | 6.7 | area | 1737 | 32083 | 34104 | 120958 | 6740 | 128468 | 103019 |
| | | mg/g DW | 0.16 | 1.59 | 1.83 | 11.06 | 0.37 | 6.8 | |
| N5/4 7 days BTH | 6.2 | area | 3518 | 71221 | 83701 | 255283 | 3762 | 115824 | 97553 |
| | | mg/g DW | 0.37 | 4.04 | 5.13 | 26.63 | 0.24 | 7 | |
| N5/4 22 days BTH | 10 | area | 17725 | 250258 | 265768 | 360298 | 14192 | 206874 | 107392 |
| | | mg/g DW | 1.04 | 7.99 | 9.17 | 21.17 | 0.5 | 7.04 | |
| N5/4 7 days WP | 7.9 | area | 1266 | 230792 | 189040 | 149745 | 8927 | 134969 | 102634 |
| | | mg/g DW | 0.1 | 9.76 | 8.64 | 11.65 | 0.42 | 6.08 | |
| N6/1 0 day BTH | 5.9 | area | 68 | 104570 | 109361 | 155436 | 6623 | 40609 | 108035 |
| | | mg/g DW | 0.01 | 5.63 | 6.36 | 15.39 | 0.4 | 2.33 | |
| N6/1 3 days BTH | 9.6 | area | 171 | 28576 | 32618 | 189668 | 7263 | 203269 | 99197 |
| | | mg/g DW | 0.01 | 1.03 | 1.27 | 12.57 | 0.29 | 7.8 | |
| N6/1 7 days BTH | 8.4 | area | 718 | 93789 | 109060 | 390133 | 7781 | 177790 | 113543 |
| | | mg/g DW | 0.05 | 3.37 | 4.24 | 25–81 | 0.31 | 6.81 | |
| N6/1 22 days BTH | 10.8 | area | 3012 | 633512 | 599460 | 426678 | 15985 | 386790 | 124721 |
| | | mg/g DW | 0.14 | 16.13 | 16.5 | 19.99 | 0.45 | 10.49 | |
| N6/2 0 day BTH | 5.7 | area | 0 | 31891 | 33610 | 73092 | 6854 | 21324 | 69201 |
| | | mg/g DW | 0 | 2.77 | 3.16 | 11.69 | 0.66 | 1.97 | |
| N6/2 3 days BTH | 6.8 | area | 0 | 21575 | 35235 | 82293 | 9340 | 90009 | 78756 |
| | | mg/g DW | 0 | 1.38 | 2.44 | 9.69 | 0.66 | 6.14 | |
| N6/2 7 days BTH | 8.5 | area | 447 | 47653 | 53238 | 290368 | 9295 | 105943 | 74862 |
| | | mg/g DW | 0.04 | 2.57 | 3.1 | 28.79 | 0.56 | 6.08 | |
| N6/7 0 day BTH | 4.8 | area | 158 | 51929 | 46536 | 102388 | 8893 | 63254 | 108621 |
| | | mg/g DW | 0.02 | 3.42 | 3.31 | 12.39 | 0.65 | 4.43 | |
| N6/7 3 days BTH | 4.9 | area | 2261 | 10420 | 13317 | 139589 | 3870 | 120264 | 117476 |
| | | mg/g DW | 0.25 | 0.62 | 0.86 | 15.3 | 0.26 | 7.63 | |
| N6/7 7 days BTH | 8 | area | 7813 | 107748 | 116835 | 464737 | 0 | 179686 | 102089 |
| | | mg/g DW | 0.61 | 4.53 | 5.3 | 35.9 | 0 | 8.04 | |
| N6/7 22 days BTH | 14.1 | area | 31445 | 609847 | 642550 | 761211 | 24765 | 601151 | 122289 |
| | | mg/g DW | 1.15 | 12.13 | 13.81 | 27.85 | 0.55 | 12.74 | |
| N6/8 0 day BTH | 6.8 | area | 40 | 49010 | 51848 | 111978 | 6328 | 26476 | 76039 |
| | | mg/g DW | 0 | 3.25 | 3.72 | 13.66 | 0.47 | 1.87 | |
| N6/8 3 days BTH | 6.1 | area | 447 | 12368 | 16802 | 74009 | 7182 | 117838 | 83366 |
| | | mg/g DW | 0.06 | 0.83 | 1.22 | 9.18 | 0.54 | 8.46 | |
| N6/8 7 days BTH | 7.9 | area | 3051 | 147316 | 164133 | 297760 | 5728 | 125094 | 89794 |
| | | mg/g DW | 0.27 | 7.12 | 8.58 | 26.48 | 0.31 | 6.44 | |

Example 31

Determination of the Inducible Drought-resistance of Transgenic Plants

Seven days after treatment with BTH or wettable powder (see example 25), the plants are taken off the irrigation system and not watered any longer. They are further grown and their phenotype is monitored. Fourteen days later BTH-treated plants had grown further and looked like irrigated control plants, whereas plants treated with wettable powder are completely dessicated. BTH-treated plants are grown further and are allowed to set seeds. Drought resistance therefore correlates with the expression of the trehalose biosynthetic genes and the accumulation of trehalose.

The above disclosed embodiments are illustrative. This disclosure of the invention will place one skilled in the art in possession of many variations of the invention. All such obvious and foreseeable variations are intended to be encompassed by the appended claims.

The invention claimed is:

1. A plant comprising in its plastid genome a first expression cassette comprising a plastid promoter operably linked to a nucleotide sequence encoding a trehalose 6-phosphate synthase and second expression cassette comprising a plastid promoter operably linked to a nucleotide sequence encoding a trehalose-6-phosphate phosphatase, wherein said plant produces trehalose.

2. A plant comprising in its plastid genome an expression cassette comprising a first nucleotide sequence encoding a trehalose 6-phosphate synthase and a second nucleotide sequence trehalose-6-phosphate phosphatase, wherein said plant produces trehalose.

3. The plant according to claim 2, wherein said first and second nucleotide sequences are transcribed from a single promoter in an operon-like polycistronic gene, wherein said promoter is capable of directing the expression of said first and second nucleotide sequences in a plastid of said plant, and wherein said plant produces trehalose.

* * * * *